(12) United States Patent
Nejad et al.

(10) Patent No.: US 11,103,686 B2
(45) Date of Patent: Aug. 31, 2021

(54) SYSTEM AND METHOD FOR MAKING MICRONEEDLES

(71) Applicant: Trustees of Tufts College, Medford, MA (US)

(72) Inventors: Hojatollah Rezaei Nejad, Boston, MA (US); Aydin Sadeqi, Boston, MA (US); Sameer Sonkusale, Boston, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 16/756,407

(22) PCT Filed: Oct. 16, 2018

(86) PCT No.: PCT/US2018/056134
§ 371 (c)(1),
(2) Date: Apr. 15, 2020

(87) PCT Pub. No.: WO2019/203888
PCT Pub. Date: Oct. 24, 2019

(65) Prior Publication Data
US 2020/0238066 A1    Jul. 30, 2020

Related U.S. Application Data

(60) Provisional application No. 62/573,094, filed on Oct. 16, 2017.

(51) Int. Cl.
*B29C 39/02* (2006.01)
*A61M 37/00* (2006.01)
(Continued)

(52) U.S. Cl.
CPC ..... *A61M 37/0015* (2013.01); *B29C 33/3842* (2013.01); *B29C 33/405* (2013.01);
(Continued)

(58) Field of Classification Search
None
See application file for complete search history.

(56) References Cited

U.S. PATENT DOCUMENTS 5,855,718 A * 1/1999 Nguyen ................ B29C 64/124
156/246
2003/0045837 A1 3/2003 Delmore
(Continued)

FOREIGN PATENT DOCUMENTS

CN    103752823    * 12/2013 ............. Y02P 10/25
JP    2008/246492   *  3/2007 .... A61M 2037/0053
(Continued)

OTHER PUBLICATIONS

JP-2008246492A (Susa) Mar. 2007 (online machine translation), [Retrieved on Oct. 29, 2020], Retrieved from: Espacenet (Year: 2007).*

(Continued)

*Primary Examiner* — Alison L Hindenlang
*Assistant Examiner* — Andrés E. Behrens, Jr.
(74) *Attorney, Agent, or Firm* — Quarles & Brady, LLP

(57) ABSTRACT

Systems and methods for creating microneedle arrays capable of delivering a suitable drug dosages to subjects are provided. In one aspect, a method comprises creating at least one forming mold using laser ablation in a cross-over line pattern. The method further comprises casting a first material onto the at least one forming mold to create at least one microneedle mold. The method further comprises casting a second material onto the at least one microneedle mold to create at least one hollow microneedle.

30 Claims, 22 Drawing Sheets

(51) Int. Cl.
  *B29C 33/40* (2006.01)
  *B29C 33/38* (2006.01)
  *B29L 31/00* (2006.01)
(52) U.S. Cl.
  CPC ..... *B29C 39/02* (2013.01); *A61M 2037/0046* (2013.01); *A61M 2037/0053* (2013.01); *B29L 2031/756* (2013.01); *B29L 2031/7544* (2013.01)

(56) References Cited

U.S. PATENT DOCUMENTS

| | | | |
|---|---|---|---|
| 2007/0191761 A1 | 8/2007 | Boone | |
| 2009/0131887 A1 | 5/2009 | Shiomitsu | |
| 2011/0177139 A1* | 7/2011 | Jung | A61K 9/0021 424/400 |
| 2015/0021830 A1* | 1/2015 | Yerazunis | B29C 64/241 264/401 |
| 2018/0009164 A1* | 1/2018 | Honda | B33Y 50/02 |
| 2018/0243952 A1* | 8/2018 | Okano | B29C 41/42 |
| 2018/0344998 A1* | 12/2018 | Ono | B29C 39/00 |

FOREIGN PATENT DOCUMENTS

| | | | |
|---|---|---|---|
| JP | 2008246492 A * | 3/2007 | ........ A61M 37/0015 |
| JP | 2008246492 A | 10/2008 | |

OTHER PUBLICATIONS

JP-200/8246492 (Susa) Mar. 2007 (online machine translation), [Retrieved on Dec. 21, 2020], Retrieved from: Espacenet (Year: 2007).*
Wilton. "How to Use Silicone Molds | Everything You Want to Know from Rosanna Pansino." YouTube, Wilton, Mar. 31, 2015, www.youtube.com/watch?v=LndyQKxUVpU. (Year: 2015).*
Tschurtschenthaler, Karl. "Reducing the Adhesion between PDMS and SU-8—Plasma Treatment of SU-8?" ResearchGate, Dec. 14, 2016, www.researchgate.net/post/Reducing-the-Adhesion-between-PDMS-and-SU-8-Plasma-treatment-of-SU-8. (Year: 2016).*
Jokinen et al. (Oxygen and nitrogen plasma hydrophilization and hydrophobic recovery of polymers, 2012) (Year: 2012).*
Mogusala, Nikita Reddy. Fabrication of Microneedle Molds and Polymer Based Biodegradable Microneedle Patches. American Journal of Drug Delivery and Therapeutics, May 6, 2015, www.imedpub.com/articles/fabrication-of-microneedle-molds-andpolymer-based-biodegradable-microneedlepatches-a-novel-method.pdf (Year: 2015).*
Park,, Jung-Hwan. "Polymer Microneedles for Controlled-Release Drug Delivery." Pharmaceutical Research, , vol. 23, No. 5, May 2006, pp. 1008-1019., doi:10.1007/s11095-006-0028-9. (Year: 2006).*
CN-103,752,823 (Liadong) Dec. 2013 (online machine translation), [Retrieved on Dec. 18, 2020], Retrieved from: Espacenet (Year: 2013).*
Chen W, et al. Microneedles as a delivery system for gene therapy. Frontiers in Pharmacology 2016; 7: 137.
Chen, M.C. et al, "Chitosan microneedle patches for sustained transdermal delivery of macromolecules," Biomacromolecules, vol. 13, No. 12, pp. 4022-4031 (2012).
Chen, M.C., et al., 2013. Fully embeddable chitosan microneedles as a sustained release depot for intradermal vaccination. Biomaterials, 34(12), pp. 3077-3086.
Juan G, et al. Preparation and characterization of mesoporous zirconia made by using a poly (methyl methacrylate) template. Nanoscale Research Letters 2008; 3: 118-122.
Foldvari, M. et al, "Non-viral gene therapy: gains and challenges of non-invasive administration methods". Journal of Controlled Release, vol. 240, pp. 165-190, 2016.
Hirai, Y. et al, "Moving mask UV lithography for three-dimensional structuring," Journal of Micromechanics and Microengineering, vol. 17, No. 2, pp. 199, 2006.

International Searching Authority, International Search Report and Written Opinion for application PCT/US2018/056134, dated Nov. 22, 2019.
Ita, K "Transdermal delivery of drugs with microneedles—potential and challenges." Pharmaceutics 7.3 (2015): 30-105.
Karimi A, et al. Fabrication and mechanical characterization of a polyvinyl alcohol sponge for tissue engineering applications. Perfusion 2014; 29: 231-237.
Khoshakhlagh, P. et al. "Development and characterization of a bioglass/chitosan composite as an injectable bone substitute," Carbohydrate polymers, vol. 157, pp. 1261-1271, Feb. 2017.
Kim, K et al., "A tapered hollow metallic microneedle array using backside exposure of SU-8," Journal of Micromechanics and Microengineering, vol. 14, No. 4, pp. 597, 2004.
Larrañeta, E. et al, "Microneedle arrays as transdermal and intradermal drug delivery systems: materials science, manufacture and commercial development," Materials Science and Engineering: R: Reports, vol. 104, pp. 1-32, 2016.
Lee, I. et al, "Formulation of two-layer dissolving polymeric microneedle patches for insulin transdermal delivery in diabetic mice," Journal of Biomedical Materials Research Part A, vol. 105, pp. 84-93, (Aug. 2017).
Maldonado, J.R. et al, "X-ray lithography: Some history, current status and future prospects," Microelectronic Engineering, vol. 161, pp. 87-93, 2016.
Mallapragada SK, et al. Crystal dissolution-controlled release systems. II. Metronidazole release from semicrystalline poly (vinyl alcohol) systems. Journal of Biomedical Materials Research 1997; 36: 125-130.
Mallapragada SK, et al. Crystal unfolding and chain disentanglement during semicrystalline polymer dissolution. AIChE Journal 1997; 43: 870-876.
Marwah H, et al. Permeation enhancer strategies in transdermal drug delivery. Drug Delivery 2016; 23: 564-578.
Moon, S.J. et al, "Fabrication of microneedle array using LIGA and hot embossing process," Microsystem Technologies, vol. 11, No. 4-5, pp. 311-318, (2005).
Murakami T, et al. Evaluation of a superior lubrication mechanism with biphasic hydrogels for artificial cartilage. Tribology International 2015; 89: 19-26.
Nejad HR, et al. Laterally Confined Microfluidic Patterning of Cells for Engineering Spatially Defined Vascularization. Small 2016; 12: 5132-5139.
Nejad HR, et al. "Low-cost and cleanroom-free fabrication of microneedles." Nature News, Nature Publishing Group, Jan. 15, 2018.
Noh T, et al. Tear force of physically crosslinked poly (vinyl alcohol) gels with different submicrometer-scale network structures. Journal of Applied Polymer Science 2015; 132: 1-6.
Otsuka E, et al. Swelling properties of physically cross-linked PVA gels prepared by a cast-drying method. Progress in Colloid Polymer Science 2009: 121-126.
Oun R, et al. A cisplatin slow-release hydrogel drug delivery system based on a formulation of the macrocycle cucurbil [7] uril, gelatin and polyvinyl alcohol. Journal of Inorganic Biochemistry 2014; 134: 100-105.
Packianather, M.S. et al, "Advanced micro and nano manufacturing technologies used in medical domain," In International Conference on the Development of Biomedical Engineering in Vietnam, pp. 637-642. Springer, Singapore, Sep. 2017.
Park, J.H. et al, "Polymer microneedles for controlled-release drug delivery," Pharmaceutical research, vol. 23, No. 5, pp. 1008-1019, 2006.
Pasparakis G, et al. Swelling studies and in vitro release of verapamil from calcium alginate and calcium alginate-ahitosan beads. International Journal of Pharmaceutics. 2006; 323: 34-42.
Prausnitz MR, et al. Transdermal drug delivery. Nature Biotechnology 2008; 26: 1261-1268.
Rad, Z.F., et al. (Oct. 9, 2017). High-fidelity replication of thermoplastic microneedles with open microfluidic ahannels. Microsystems & Nanoengineering, 3, p. 17034.

(56) References Cited

OTHER PUBLICATIONS

Sadeqi, A., et al. "Cost-effective fabrication of chitosan microneedles for transdermal drug delivery." IEEE conference Publication. IEEE.org, Jul. 21, 2018.

Sullivan, S.P. et al, "Minimally invasive protein delivery with rapidly dissolving polymer microneedles," Advanced materials, vol. 20, No. 5, pp. 933-938, 2008.

Takahashi, H., et al., 2016. Scalable fabrication of microneedle arrays via spatially controlled UV exposure. Microsystems & Nanoengineering, 2, p. 16049.

Takamura A, et al. Drug release from poly (vinyl alcohol) gel prepared by freeze-thaw procedure. Journal of controlled Release. 1992; 20: 21-27.

Vinayakumar, K.B. et al, "A hollow stainless steel microneedle array to deliver insulin to a diabetic rat," Journal of Micromechanics and Microengineering, vol. 26, No. 6, 2016.

Wang, Qi Lei, et al. "A fabrication method of microneedle molds with controlled microstructures."C, Elsevier, Apr. 13, 2016.

\* cited by examiner

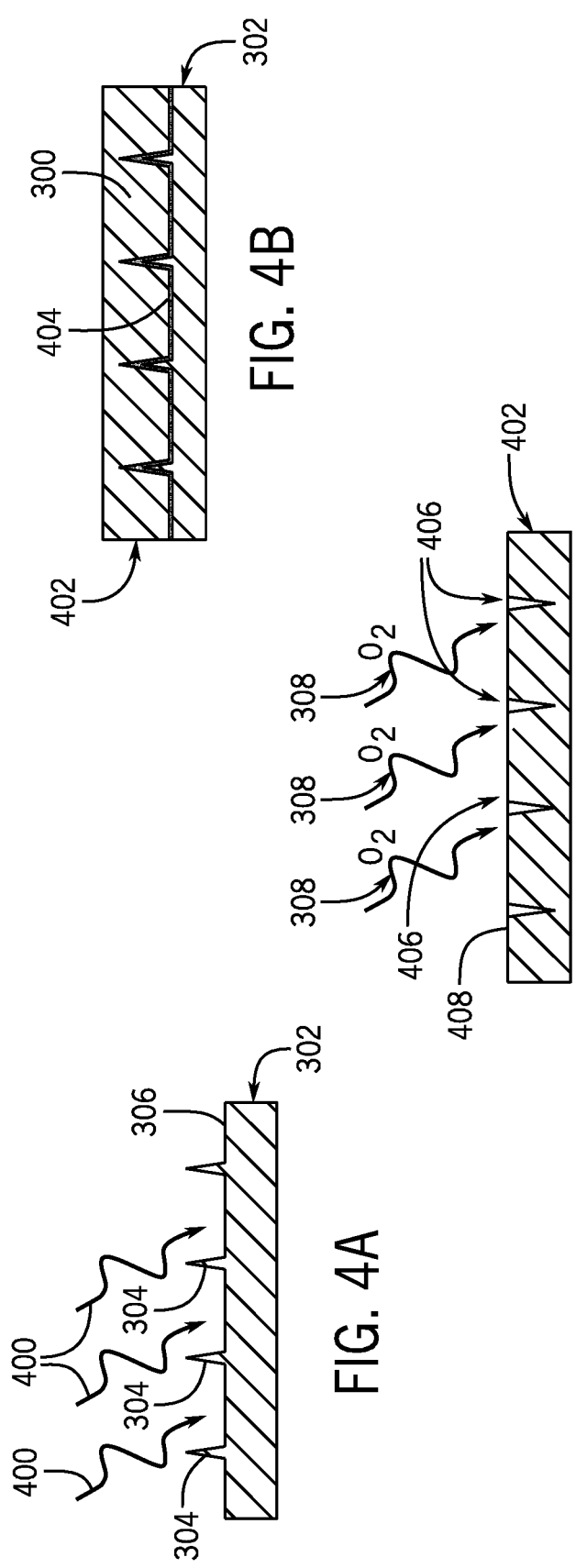

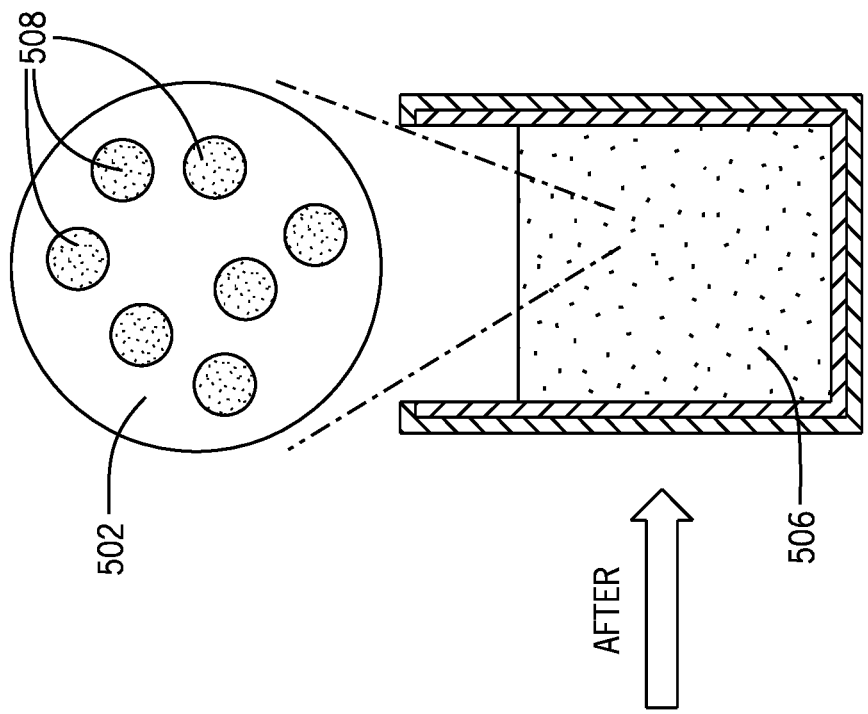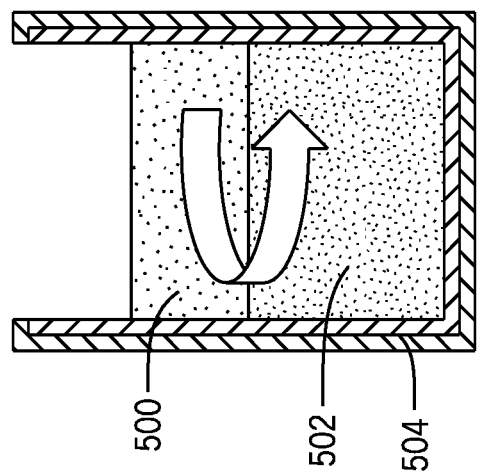

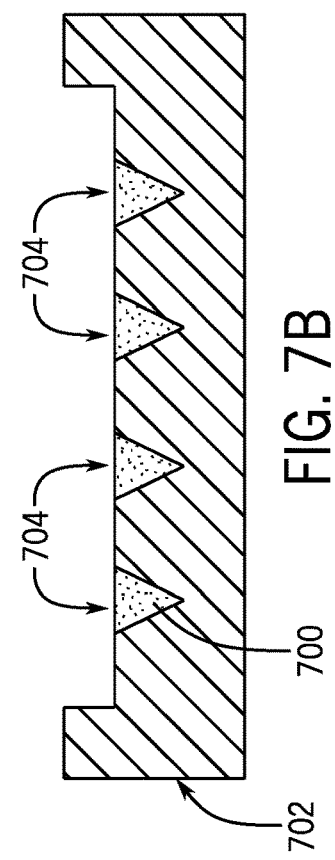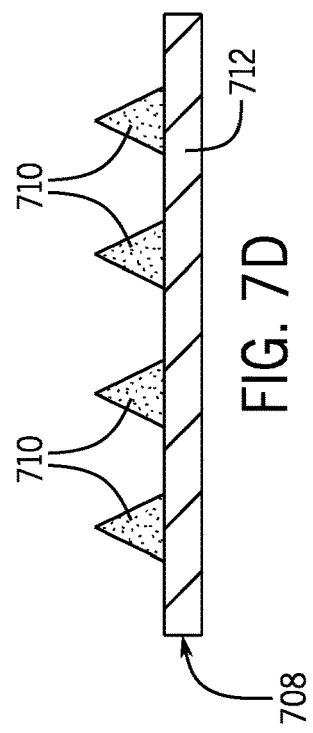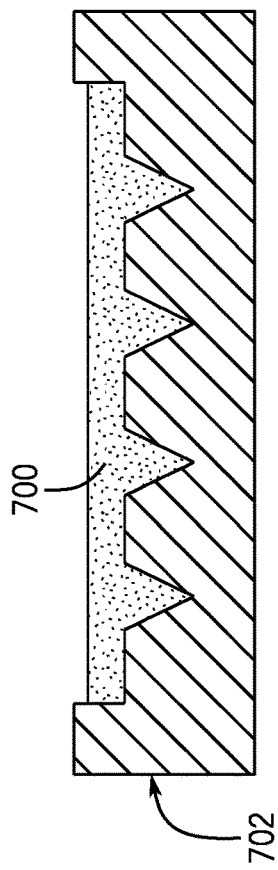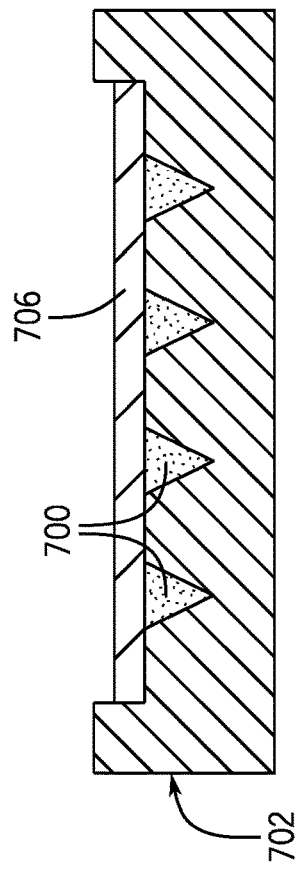
FIG. 7A
FIG. 7B
FIG. 7C
FIG. 7D

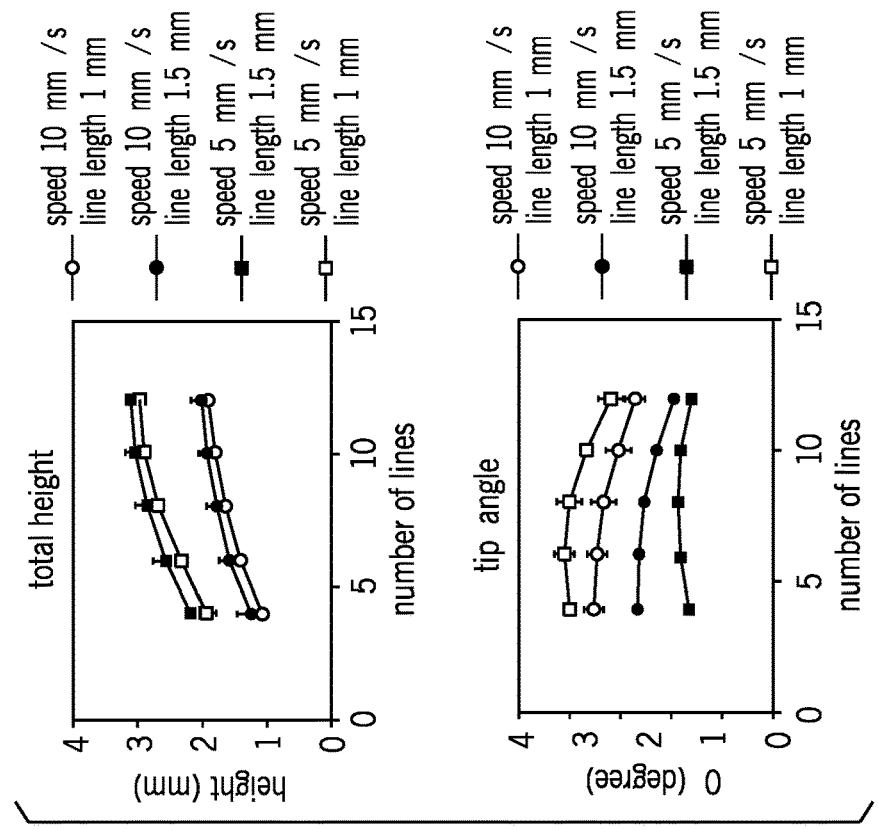
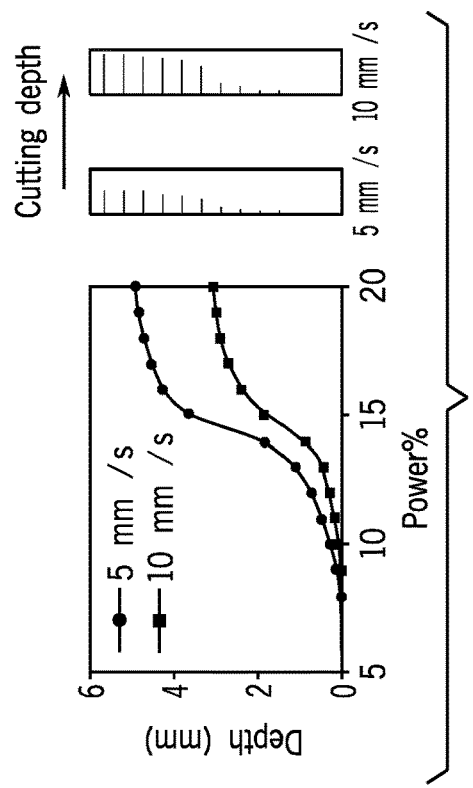
FIG. 12A
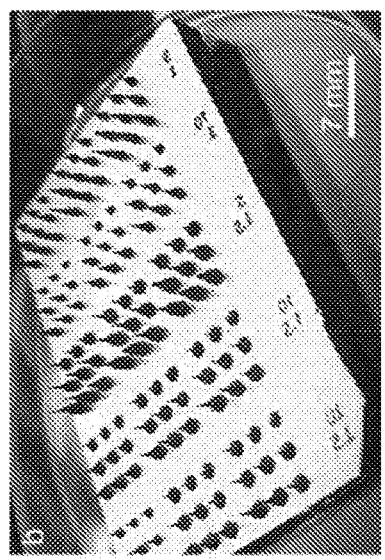
FIG. 12B
FIG. 12C

Fine Microneedles

SYSTEM AND METHOD FOR MAKING MICRONEEDLES

CROSS-REFERENCE TO RELATED APPLICATIONS

This application represents the U.S. national stage entry of PCT/US2018/056134, filed Oct. 16, 2018, which claims benefit of U.S. Provisional Patent Application 62/573,094 filed Oct. 16, 2017. The contents of these applications are hereby incorporated by reference as set forth in their entirety herein.

STATEMENT REGARDING FEDERALLY SPONSORED RESEARCH

This invention was made with government support under grant N0014-16-1-2550 awarded by the United States Navy. The government has certain rights in the invention.

BACKGROUND

Skin is considered as the largest organ in the body with around 1.5 $m^2$ surface area in adults and it can be a desirable administration route for drugs. However, the outermost layer of skin, stratum corneum, which protects the human body from toxic chemicals, makes it challenging for high molecular weight and hydrophilic molecules to pass through this membrane. Among different approaches to enhance the transdermal drug delivery, the use of microneedles as a non-invasive method is a promising approach to increase the permeability of the skin to drugs.

Unlike hypodermic needles, microneedles allow for a painless and non-invasive method of drug administration, are safe after use, and have a low disposal cost. Microneedles create microchannels in the skin, which allow for drug molecules to transport easily through them into the dermis. Different studies have shown that intradermal administration of specific drugs using microneedles increases the therapeutic efficacy compared to the intramuscular and the subcutaneous routes. Thus, microneedles can provide a route for transdermal drug delivery for molecules that are not readily absorbed topically.

A challenge during fabrication of microneedle is to achieve uniformity and reproducibility of the needle geometry at the micron scale resolution to facilitate penetration of the needles in the skin. Microfabrication techniques using standard lithography are very promising in this regard. However, fabrication of microneedles has traditionally been very challenging, mainly due to the 3D conical geometry and the high aspect ratio structures of the microneedles (the height of microneedles varies from 0.5 mm to 3 mm).

Microneedles are fabricated most commonly using molding methods, where the molds are prepared using complicated microfabrication procedures in a cleanroom. These procedures include, photolithography using deep X-ray lithography of Lithographie, Galvanoformung, Abformung (LIGA), and ultraviolet (UV) lithography. These methods, however, are very time consuming and require advanced cleanroom facilities, making them expensive, if not cost prohibitive for general drug delivery.

SUMMARY

The present disclosure overcomes the aforementioned drawbacks by providing systems and methods for creating efficient, cleanroom-free microneedle arrays capable of delivering a suitable drug dosage to a subject. The systems and methods provided herein can be achieved in a cost and time efficient manner compared to traditional systems and methods.

In accordance with one aspect of the disclosure, a method for producing microneedles is provided. The method comprises creating at least one forming mold using laser ablation in a cross-over line pattern. The method further comprises casting a first material onto the at least one forming mold to create at least one microneedle mold. The method further comprises casting a second material onto the at least one microneedle mold to create at least one hollow microneedle.

In some instances, the cross-over line pattern may allow for the at least one forming mold, and thereby the at least one microneedle mold and the at least one hollow microneedle, to have a conical shape. The method may further comprise plasma treating the at least one microneedle mold prior to casting the second material onto the at least one microneedle mold. The method may further comprise heating the at least one hollow microneedle and the at least one microneedle mold to dry the at least one hollow microneedle. The method may further comprise cooling the at least one microneedle mold and the at least one hollow microneedle to further dry and harden the at least one hollow microneedle. The second material may be at least one of biocompatible, bioresorbable, non-antigenic, and nontoxic. The second material may be at least one of chitosan polybutylene adipate terephthalate (PBAT), and poly(butylene adipate-co-terephthalate). The first material may be polydimethylsiloxane.

In accordance with another aspect of the disclosure, a method for producing microneedles is provided. The method comprises creating at least one microneedle mold using laser ablation in a cross-over line pattern. The method further comprises casting a material onto the at least one microneedle mold to create at least one microneedle.

In some instances, the material may be a macroporous structured hard material. The material may be an emulsified, homogeneous mixture of a photocurable biocompatible resin and at least one of a concentrated drug solution and a dried drug powder.

In some instances, creating the at least one microneedle mold using laser ablation in a cross over lines pattern may comprise creating at least one primary forming mold using laser ablation in the cross-over line pattern, casting a second material onto the at least one primary forming mold to create at least one secondary forming mold, casting the second material onto the at least one secondary forming mold to create the at least one microneedle mold, and removing the at least one microneedle mold from the at least one secondary forming mold.

In some instances, the method may further comprise plasma treating and silanizing the at least one secondary forming mold. The second material may be a stretchable polymer. The method may further comprise placing the at least one microneedle and the at least one microneedle mold under vacuum to densify the at least one microneedle.

In accordance with another aspect of the disclosure, a flexible microneedle patch is provided. The flexible microneedle patch comprises a flexible patch and at least one microneedle. The flexible patch is configured to conform to a portion of a subject. The at least one microneedle is coupled to the flexible patch. The at least one microneedle is configured to administer a drug solution to the subject when the flexible patch is conformed to the subject.

In some instances, the flexible patch may include an embedded electronic chip configured for wireless communication and data transfer. The flexible patch may be detectable and traceable. The flexible patch may include at least one sensor configured to monitor a drug release rate. The at least one sensor and the embedded electronics may cooperatively allow for the monitoring of drug release of the drug solution. The at least one microneedle may comprise a macroporous structured hard material.

The foregoing and other advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 4A is a cross-sectional view of the microneedle protrusion mold of FIG. 3B being silanized.

FIG. 4B is a cross-sectional view of the first material being cast onto the silanized microneedle protrusion mold of FIG. 4B to create a microneedle cavity mold.

FIG. 4C is a cross-sectional view of the microneedle cavity mold of FIG. 4B being plasma treated.

FIG. 4D is a cross-sectional view of the second material being cast onto the microneedle cavity mold of FIG. 4C to create a solid microneedle array.

FIG. 4E is a cross-section view of the solid microneedle array.

FIG. 5A is a schematic view of a container holding a drug solution and a polymer liquid.

FIG. 5B is a schematic view of an emulsified composite solution of the drug solution and the polymer liquid.

FIG. 7A is a cross-sectional view of a material being cast onto a microneedle cavity mold to create a microneedle array.

FIG. 7B is a cross-sectional view of the microneedle array within the microneedle cavity mold of FIG. 7A, with the excess material removed from the microneedle array.

FIG. 7C is a cross-sectional view of the microneedle array within the microneedle cavity mold of FIG. 7B, with a flexible patch attached to the microneedle array to create a flexible microneedle patch.

FIG. 7D is a cross-sectional view of the flexible microneedle patch of FIG. 7C.

FIG. 12A is a chart showing the depth of engraving with various powers and speeds of laser engraving.

FIG. 12B is an image depicting different sizes of needles resulting from different settings of laser power and speed.

FIG. 12C is a chart showing the different height and tip angle of the needles depending on the speed (first number in the legend) and length of lines in millimeter (second number in the legend after dash).

FIG. 16J is a chart showing FTIR results for non-crosslinked and crosslinked PVA (PVA microneedle patch).

DETAILED DESCRIPTION

As disclosed herein, systems and methods for manufacturing microneedles are provided. In one aspect, a facile, efficient, low-cost, and cleanroom-free technique for the fabrication of microneedles is provided. Microneedles maybe created using molds formed using laser ablation. A microneedle mold with high-aspect ratios can be formed on acrylic sheets, for example, by engraving a pattern of cross over lines (COL). The COL may be engraved using CO2 laser cutter. Ablating a COL pattern on an acrylic sheet can create a sharp, conical-shape that may be located, for example, in the center of the design.

In one method, the laser beam may be passed over the same point several times while engraving (ablation). During each pass, the beam may follow a different path to achieve a high aspect ratio. This method can be used to fabricate microneedle molds with different dimensions (depth, shape, and tip angle). These molds can be used to fabricate degradable microneedle patches with a variety of materials.

Figure 1:
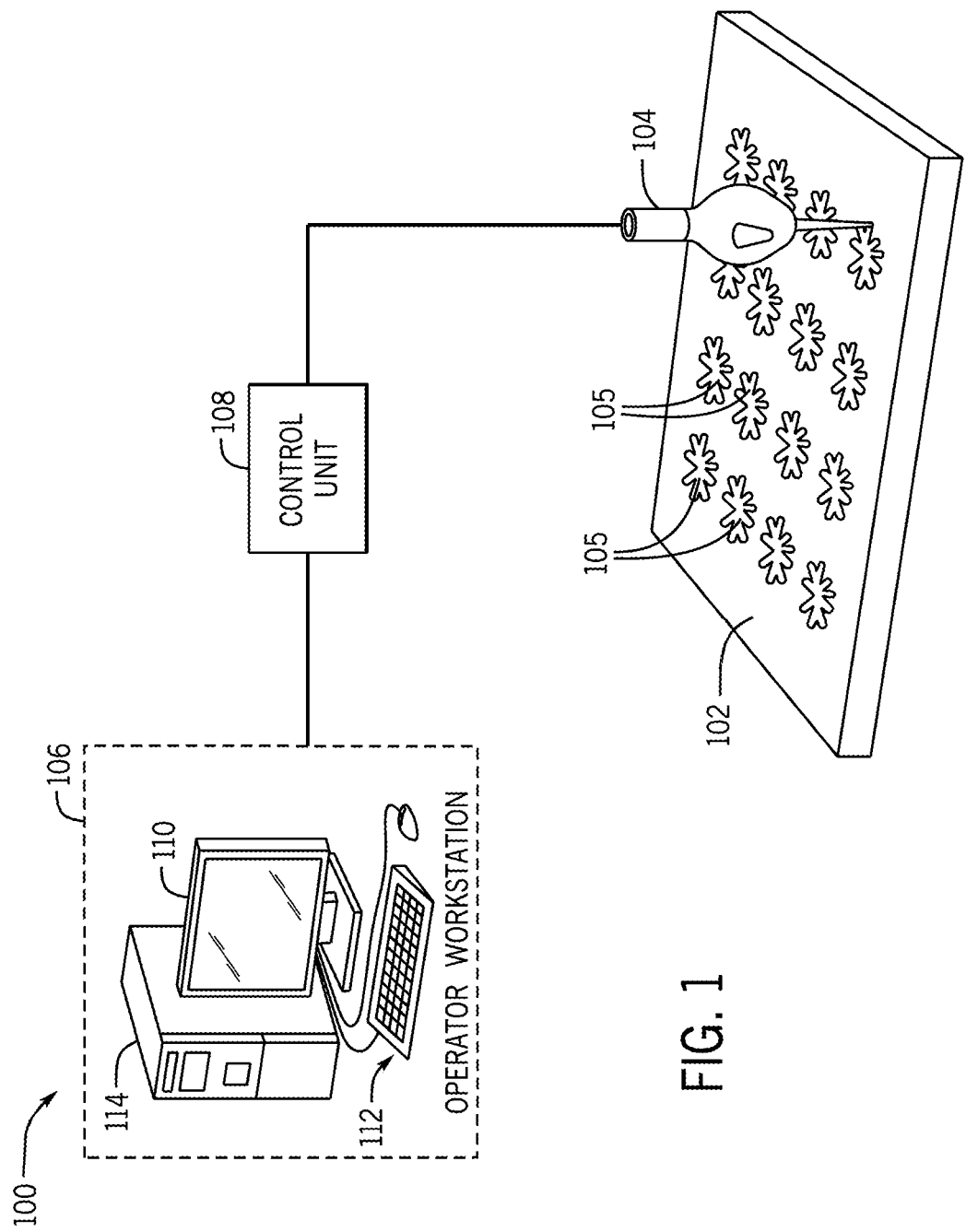
FIG. 1 is a perspective view of microneedle mold forming system, in accordance with aspects of the present disclosure.

Referring to FIG. 1, an exemplary cross over lines (COL) system 100 is provided that is configured to produce a microneedle-forming mold 102 using a laser cutter 104 in a cross over lines pattern, as described below. The microneedle-forming mold 102 can include a plurality of microneedle-forming cavities 105, each created using the cross over lines pattern. In the illustrated, non-limiting example, the microneedle-forming mold 102 includes sixteen evenly-spaced microneedle-forming cavities 105. In other instances, the microneedle-forming mold 102 can include any number of microneedle-forming cavities as necessary for a given application.

The microneedle-forming mold 102 may comprise an acrylic material. For example, in some instances, the microneedle-forming mold 102 may be formed from a clear cast acrylic sheet. However, in some other instances, the microneedle-forming mold 102 may comprise other materials.

For example, in some instances, the microneedle-forming mold 102 may comprise a plastic material, such as, for example, acrylonitrile butadiene styrene (ABS), acrylic (Plexiglas, Lucite, PMMA), Delrin (POM, acetal), Kapton tape (polyimide), Mylar (polyester), or polyethylene terephthalate glycol (PETG). In some instances, the microneedle-forming mold 102 may comprise a foam material, such as, for example, ethylene-vinyl acetate or Depron foam. In some instances, the microneedle-forming mold 102 may comprise a metallic material, such as, for example, steel, copper, or aluminum. In some instances, the microneedle-forming mold 102 may comprise a magnetic sheet, a paper material, a rubber material, polytetrafluoroethylene (PTFE or Teflon), or a cloth material (e.g., leather, suede, felt, hemp, or cotton). In some other instances, the microneedle-forming mold 102 may comprise any other material having a suitable FTIR transmission spectrum for a selected laser cutter.

The laser cutter 104 may be a carbon dioxide ($CO_2$) laser cutter. In some instances, the laser cutter 104 may have a power of, for example, 60W, for example, as a maximum. In some other instances, the laser cutter 104 may have a maximum power between 30W and 140W.

The COL system 100 may include an operator workstation 106 and a control unit 108. The operator workstation 106 may include a display 110, one or more input devices 112 (e.g., a keyboard, a mouse), and a processor 114. The processor 114 may include a commercially available programmable machine running a commercially available operating system. The operator workstation 106 provides an operator interface that facilitates entering laser cutting patterns and parameters into the COL system 100 that may be communicated to the control unit 108. The control unit 108 is configured to control operation of the laser cutter 104 while forming the microneedle-forming mold 102.

Figure 2A:
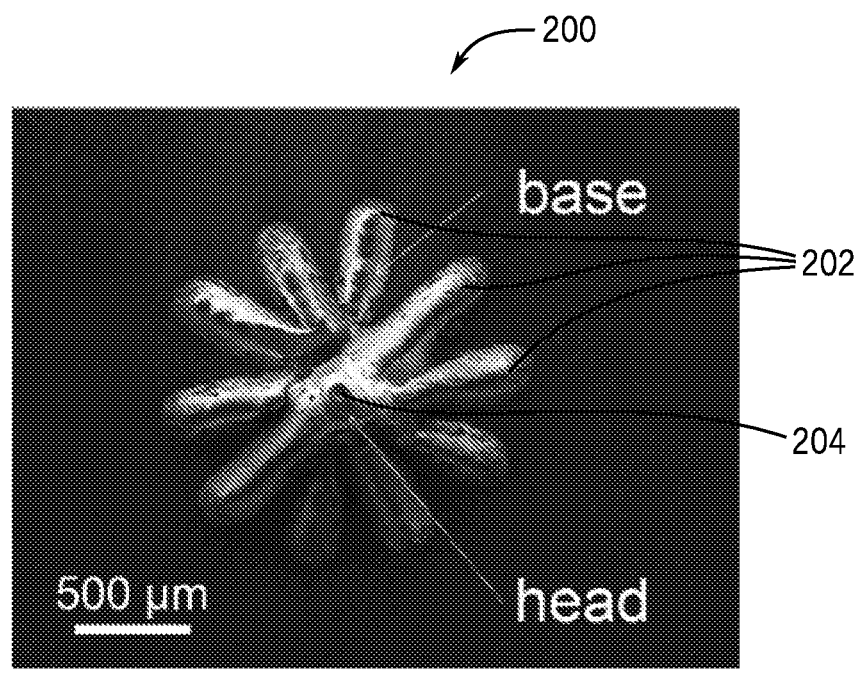
FIG. 2A is a plan view of a forming mold cavity created using a cross over lines (COL) technique with the microneedle mold forming system of FIG. 1A.
Figure 2B:
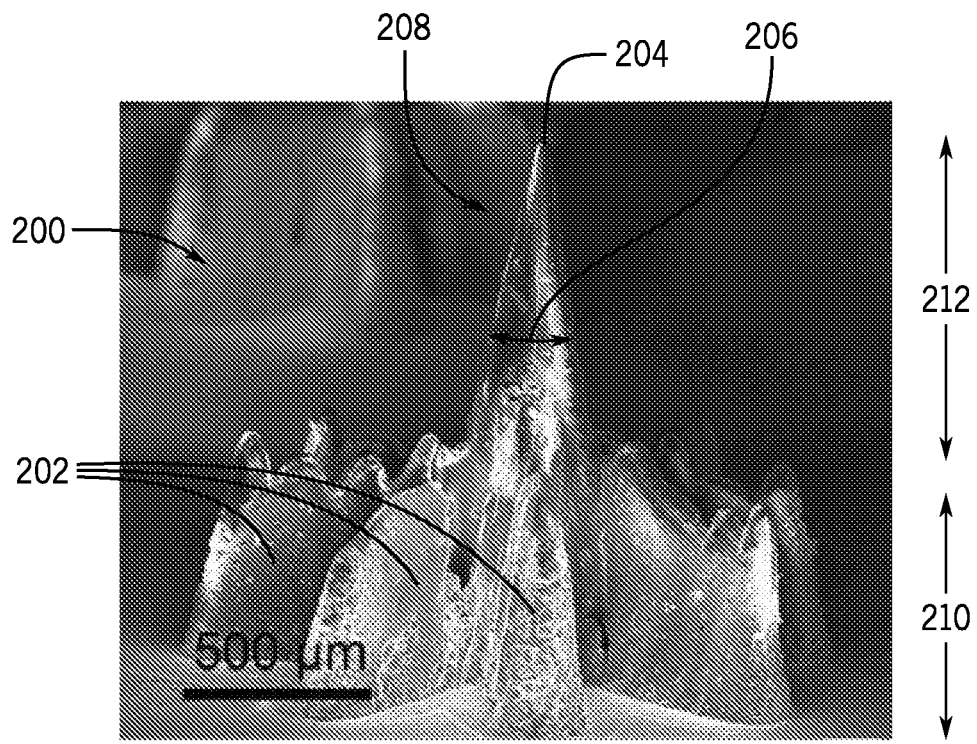
FIG. 2B is a side view of the forming mold cavity of FIG. 1B.

Referring now to FIGS. 2A and 2B, a microneedle-forming cavity 105 of the microneedle-forming mold 102 is illustrated. During fabrication of the microneedle-forming mold 102, the laser cutter 104 can be used to cut or engrave cross lines 202 that overlap only at their center cross point 204. As the laser cutter 104 passes the center cross point 204 with each cross line 202, a sharp cone takes shape at the center cross point 204, thereby forming the microneedle-forming cavity 105.

Because the center cross point 204 is traversed with each cross line 202, the depth of the center cross point 204 is proportional to number of times the laser cutter 104 passes through the center cross point 204. Said differently, the depth of the center cross point 204 is proportional to the number of cross lines 202 created. Accordingly, the depth of the microneedle-forming mold 102 can be adjusted by changing the number of cross lines 202 used in the COL pattern.

Additionally, a tip angle 206 of the cavity tip 208 may be adjusted by the scanning speed of the laser cutter 104 engraving each of the cross lines 202. Further, a length of each of the cross lines 202 may affect the consistency of the depth and/or tip angle of each microneedle-forming cavity 105. For example, longer cross lines 202 may allow for the laser cutter 104 to achieve a more consistent speed when traversing the center cross point 204 during each pass, thereby allowing for a more consistent depth and/or tip angle of the cross lines 202.

Thus, a specific aspect ratio (such as, a width to depth ratio) of the microneedle-forming cavity 105 can be achieved by selecting a corresponding laser scanning speed, number of cross lines 202, and length of each cross line 202 to create microneedles of a given size and shape, as will be discussed below.

Figure 2C:
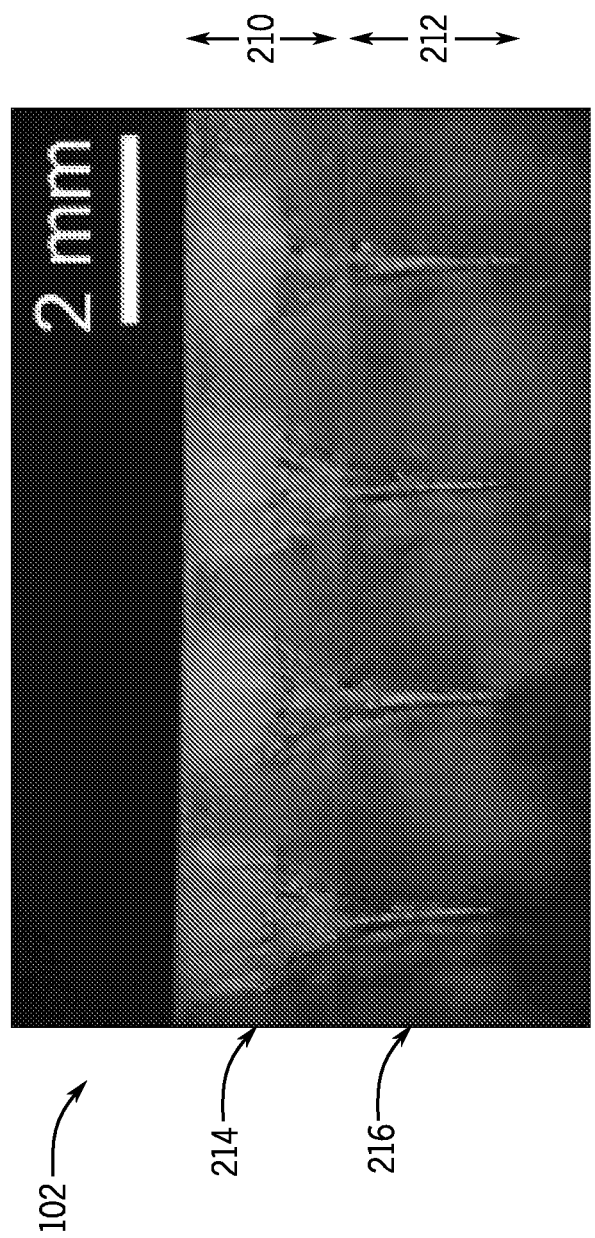
FIG. 2C is a cross-sectional view of a microneedle-forming mold created using the microneedle mold forming system of FIG. 1.

Additionally, due to the COL technique, after the laser cutting process described above, the microneedle-forming cavity 105 can include a base 210 and a head 212, as shown in FIGS. 2B and 2C. The base 210 can define a star shape due to the pattern of the cross lines 202. In some instances, the star shape may not be desired for certain applications. Conversely, the head 212 can define a fine, conical shape suitable for microneedle application. Accordingly, the base 210 may be removed from the head 212, such that the microneedle-forming cavity 105 comprises only a fine, conical shape. In some instances, this may be done by grinding or cutting the base 210 from the head 212.

In some other instances, the microneedle-forming mold 102 may comprise a top sheet 214 and a bottom sheet 216 that are stacked together, as shown in FIG. 2C. The top sheet 214 may be provided with a thickness corresponding to the thickness or depth of the base 210. As such, once the microneedle-forming cavity 105 is created, the top sheet 214 may be removed from the bottom sheet 216, leaving just the cone-shaped head 212 of the microneedle-forming mold 102.

Figure 3B:
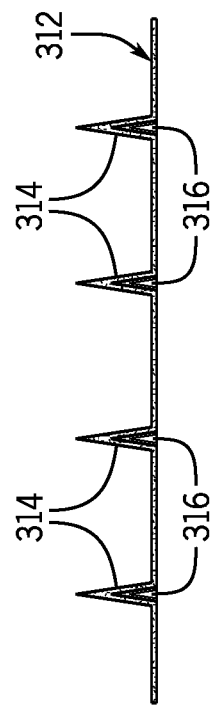
FIG. 3B is a cross-sectional view of the microneedle protrusion mold of FIG. 3A being plasma treated.
Figure 3D:
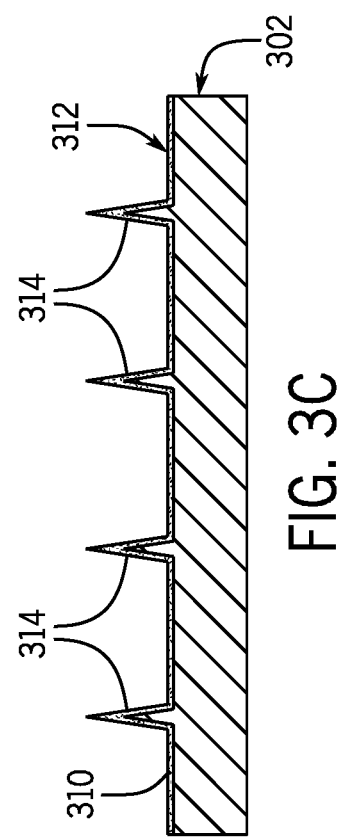
FIG. 3D is a cross-sectional view of the hollow microneedle array of FIG. 3C.
Figure 3A:
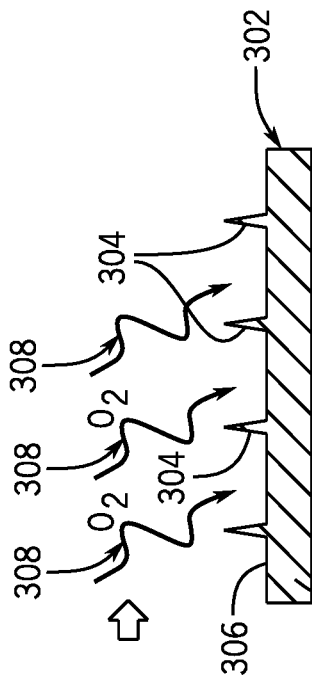
FIG. 3A is a cross-sectional view of the microneedle-forming mold of FIG. 2C, with a first material cast onto the microneedle-forming mold to form a microneedle protrusion mold.

Referring now to FIGS. 3A-3D, one non-limiting process for creating a hollow microneedle array is illustrated. After creating the microneedle-forming mold 102, a first moldable material 300 may be cast onto the microneedle-forming mold 102, as shown in FIG. 3A.

In some instances, the first moldable material 300 may comprise an elastomeric material. For example, the first moldable material 300 may comprise polydimethylsiloxane (PDMS). In some other instances, the first moldable material 300 may comprise polybutylene adipate terephthalate (PBAT), poly(butylene adipate-co-terephthalate), or any other suitable material. In some instances, the first foldable material 300 may have a 10:1 weight ratio of elastomer to curing agent. In some other instances, the first foldable material 300 may have a 1:1 weight ratio of elastomer to curing agent.

The first moldable material 300 may then be allowed to dry, thereby forming a microneedle protrusion mold 302, which may then be removed from the microneedle-forming mold 102, as shown in FIG. 3B. As illustrated, the microneedle protrusion mold 302 includes a plurality of microneedles 304 protruding from a surface 306 thereof. The plurality of microneedles 304 may correspond in size and shape to the microneedle-forming cavities 105 of the microneedle-forming mold 102.

With continued reference to FIG. 3B, each of the plurality of microneedles 304 and the top surface 306 may be activated by applying plasma 308 thereto. In some instances, the plasma 308 may be oxygen plasma. In some other instances, the plasma 308 could be air plasma, nitrogen plasma, or any other suitable type of plasma treating.

Figure 3C:
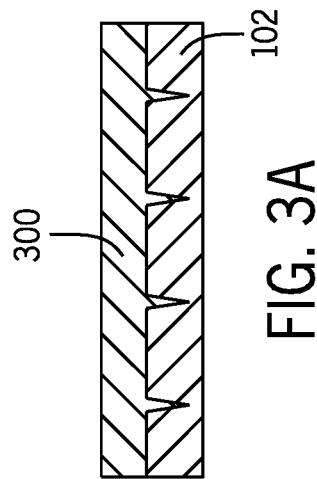
FIG. 3C is a cross-sectional view of a second material being cast onto the microneedle protrusion mold of FIG. 3B to create a hollow microneedle array.

A second moldable material 310 may then be cast onto the microneedle protrusion mold 302, as shown in FIG. 3C. The second moldable material 310 may be at least one of biocompatible, bioresorbable, non-antigenic, and nontoxic. In some instances, the second moldable material 310 may comprise a polycationic polymer and may have at least a drug solution mixed therein. For example, in some instances, the second moldable material 310 may comprise a chitosan solution. In some other instances, the second moldable material 310 may comprise polyethylene glycol (PEG), poly(ethylene glycol) diacrylate (PEGDA), gelatin, gelatin methacryloyl (GelMA), polyvinyl alcohol (PVA), silk, or any other suitable material.

In the instances where the second moldable material 310 comprises a chitosan solution, the chitosan solution may comprise a chitosan powder being dissolved in a 1% (volume/volume) aqueous solution of acetic acid to obtain a 2% (weight/volume) chitosan solution. In some instances, the chitosan solution may be initially viscous. Accordingly, the chitosan may be subsequently dialyzed at room temperature against deionized (DI) water, including several water exchanges, to remove excess acetic acid. In some instances a final pH of approximately 6.0 may be desirable. The near-neutral chitosan solution may then be purified by filtration, and water may be subsequently evaporated until the concentration of the chitosan solution is approximately 5% weight, which may result in a viscous hydrogel. This concentrated chitosan hydrogel solution may then be used for the casting process. A drug solution may then be added to the concentrated chitosan hydrogel solution.

Plasma treating the top surface 306 of the microneedle protrusion mold 302 prior to casting the second moldable material 310 creates a hydrophilic surface that facilitates flow of the second moldable material 310 over the microneedle protrusion mold 302 during the casting process, thereby allowing for a more accurate casting process.

The second moldable material 310 may then be allowed to dry, thereby creating a hollow microneedle array 312 including a plurality of hollow microneedles 314. Similarly, the plurality of hollow microneedles 314 may correspond in size and shape to the plurality of microneedles 304 of the microneedle protrusion mold 302, and therefore also to the plurality of microneedle-forming cavities 105 of the microneedle-forming mold 102.

In some instances, the microneedle protrusion mold 302 and the hollow microneedle array 312 may be placed under vacuum pressure while the hollow microneedle array 312 dries. The application of vacuum pressure may concentrate the second moldable material 310 by removing any gaseous bubbles and densifying the second moldable material 310.

In some instances, to aid in the drying of the hollow microneedle array 312, the microneedle protrusion mold 302 and the hollow microneedle array 312 can be heated. For example, in some instances, the microneedle protrusion mold 302 and the hollow microneedle array 312 may be placed on a hot plate together to further dry the hollow microneedle array 312.

Once the hollow microneedle array 312 has dried, the microneedle protrusion mold 302 and the hollow microneedle array 312 may then be cooled. Cooling the microneedle protrusion mold 302 and the hollow microneedle array 312 may further harden the hollow microneedle array 312, while simultaneously shrinking the microneedle protrusion mold 302, thereby easing removal of the hollow microneedle array 312 from the microneedle protrusion mold 302.

The hollow microneedle array 312 may then be removed from the microneedle protrusion mold 302 and loaded with a drug solution 316, as shown in FIG. 3D. In some instances, to load the drug solution 316, a reservoir (not shown) may be attached to the hollow microneedle array 312. The drug solution 316 may flow through the hollow microneedles 314 either diffusively, passively (using capillary action once the tips of the hollow microneedles are absorbed into the skin), or selectively (using a pressure source to selectively pressurize and administer the drug solution 316). In some instances, the pressure source could be the subject pressurizing the reservoir by squeezing or pushing on the reservoir. In some other instances, the pressure source could be a separate pressure pump.

The loaded hollow microneedle array 312 may then be applied to the skin of a subject. As the hollow microneedle array 312 is absorbed into the skin, the drug solution 316 can be administered to the subject transdermally.

The amount of the drug solution 316 administered to the subject may be proportional to the internal volume of the plurality of hollow microneedles 314. Thus, controlling the size and shape of the microneedle-forming cavities 105 of the microneedle-forming mold 102, which, as discusses above, corresponds to the resulting size and shape of the plurality of hollow microneedles 314, the amount of drug administered to the subject can be predetermined by altering the COL parameters discussed above.

Referring now to FIGS. 4A-4E, a process for creating a solid microneedle array is illustrated. The beginning of the process for creating a solid microneedle array is identical to the process for creating the hollow microneedle array described above. Specifically, the microneedle protrusion mold 302 is created in the same manner, and is subsequently plasma treated, as described above.

After plasma treating the microneedle protrusion mold 302 (illustrated in FIG. 3B), the microneedle protrusion mold 302 may then be silanized by applying a silanizing solution 400 to each of the plurality of microneedles 304 and the top surface 306, as shown in FIG. 4A. For example, the microneedle protrusion mold may be silanized using Tricholor (1H, 1H, 2H, 2H-perfluorooctyl) silane.

In some instances, the microneedle protrusion mold 302 may be silanized under vacuum, such as, for example, inside a desiccator.

After silanizing the microneedle protrusion mold 302, the first moldable material 300 may then be cast onto the microneedle protrusion mold 302. The first moldable material 300 may then be allowed to dry, thereby forming a microneedle cavity mold 402. The silanization of the microneedle protrusion mold 302 provides a silanized layer 404 between the microneedle protrusion mold 302 and the microneedle cavity mold 402 during the casting process, as shown in FIG. 4B. The silanized layer 404 prevents the microneedle protrusion mold 302 and the microneedle cavity mold 402, which may both be made of the first moldable material 300, from bonding to each other. Accordingly, the silanized layer 404 can be used to increase the ease with which the microneedle cavity mold 402 may be removed from the microneedle protrusion mold 302 once the microneedle cavity mold 402 has dried.

As shown in FIG. 4C, the microneedle cavity mold 402 has been removed from the microneedle protrusion mold 302, the microneedle cavity mold 402 includes a plurality of microneedle cavities 406 extending into a surface 408 of the microneedle cavity mold 402. The plurality of microneedle cavities 406 may correspond in size and shape to the plurality of microneedles 304 of the microneedle protrusion mold 302. Similar to the microneedle protrusion mold 302, each of the plurality of microneedle cavities 406 and the surface 408 may then be activated by applying the plasma 308 thereto.

The second moldable material 310 may then be cast onto the microneedle cavity mold 402, as shown in FIG. 4D. The plasma treatment of the plurality of microneedle cavities 406 and the surface 408 prior to casting the second moldable material 310 similarly creates a hydrophilic surface that facilitates the flow of the second moldable material 310 over the microneedle cavity mold 402 and into each of the plurality of microneedle cavities 406 during the casting process, thereby allowing for a more accurate casting process.

The second moldable material 310 may then be allowed to dry, thereby creating a solid microneedle array 410 including a plurality of solid microneedles 412. The plurality of solid microneedles 412 may similarly correspond in size and shape to the plurality of microneedles 304 of the microneedle protrusion mold 302. In some instances, the microneedle cavity mold 402 and the solid microneedle array 410 may be placed under vacuum pressure while the solid microneedle array 410 dries to concentrate the second moldable material 310, as described above.

Similarly, to aid in the drying of the solid microneedle array 410, the microneedle cavity mold 402 and the solid microneedle array 410 may be heated. For example, the microneedle cavity mold 402 and the solid microneedle array 410 may be placed together on a hot plate to further dry the solid microneedle array 410.

Referring now to FIG. 4E, the solid microneedle array 410 may be removed from the microneedle cavity mold 402. The solid microneedle array 410 may then be applied to the skin of a subject. As mentioned above, a drug solution may be added to and mixed into the second moldable material 310 prior to the casting of the solid microneedle array 410. Thus, as the plurality of solid microneedles 412 are absorbed by the skin, the drug solution held within the second moldable material 310 is administered to the subject transdermally. Accordingly, the amount of drug solution administered to the subject is proportional to the amount of drug solution mixed into the second moldable material 310 and the size and shape of the plurality of solid microneedles 412.

Alternatively or additionally, the solid microneedle array 410 may be coated with the drug solution prior to applying the solid microneedle array 410 to the skin of the subject, thereby increasing the amount of the drug solution administered to the subject. Also, it will be appreciated that the methods described above may be performed with a variety of differing materials that are suitable for use as a microneedle array to be used for the transdermal delivery of drugs.

Traditional drug delivery microneedles have generally fallen into four classifications: solid, coated, dissolving, and hollow. Meanwhile, the traditional materials used to create microneedles can generally be divided into two main categories, including microneedles made out of soft materials (having elastic moduli close to that of skin, e.g., hydrogels) and microneedles composed of hard materials (having elastic moduli much larger than that of skin e.g., stainless steel or hard resins).

Hard microneedles have much higher young's modulus when compared to skin, and therefore can effectively penetrate into different skin types. However, due to the inherent nature of the materials, drugs may not always be loaded into the microneedles. Instead, for hard microneedles, the drug may be delivered as a coating on the microneedles or by applying the drug on top of the pores created by microneedles. However, when coating the microneedles, the delivery dosage may be too small for some applications. Similarly, when the drug is delivered on top of pores created by the microneedles, the delivery rate may be too low for some applications. Accordingly, it is can be difficult to deliver a meaningful drug dosage using hard needles.

Conversely, soft materials may be capable of delivering meaningful (high) drug dosages, because the drug can be embedded inside microneedles through mixing with the pre-casting material solution. The drug release, upon penetration, can occur through diffusion of the drug from the microneedles (hydrogel-forming needles) or dissolution/degradation of microneedles into the skin (dissolving microneedles). However, as a general problem, many soft microneedles, in fact, do not effectively penetrate into the skin, or, in some cases, have considerable variability when used on different skin types. Further, drug assembly into the soft materials may create an interaction of the drug and the material matrix, which may affect the release profile or drug efficacy.

FIGS. 5A and 5B show a process for preparing an emulsified composite solution. The emulsified composite solution can be used to create a macroporous structured hard (macroPoSH) microneedle array comprising a plurality of macroPoSH microneedles, which are hard enough to effectively penetrate the skin of a subject, while still providing a meaningful drug dosage.

Specifically, a drug solution 500 and a polymer liquid 502 may first be added to a container 504, as shown in FIG. 5A. The drug solution 500 may then be emulsified into the polymer liquid 502. Emulsifying the drug solution 500 into the polymer liquid 502 results in an emulsified composite solution 506 containing a plurality of drug solution micro-droplets 508 dispersed homogenously throughout the polymer liquid 502, as shown in FIG. 5B. The polymer liquid 502 selected may be chosen such that, once the emulsified composite solution 506 sets or dries, the solid macroPoSH material created has a Young's modulus significantly higher than that of human skin. For example, in some instances, the solid macroPoSH material may have a Young's Modulus between ten and one thousand times that of human skin.

The mechanical properties of skin may vary significantly from person to person depending on a multitude of factors, such as, for example, age, race, life style, hydration, and various other factors. Thus, the Young's modulus of the skin of the subject may be between approximately 0.05 MPa and 1 MPa.

Figure 6B:
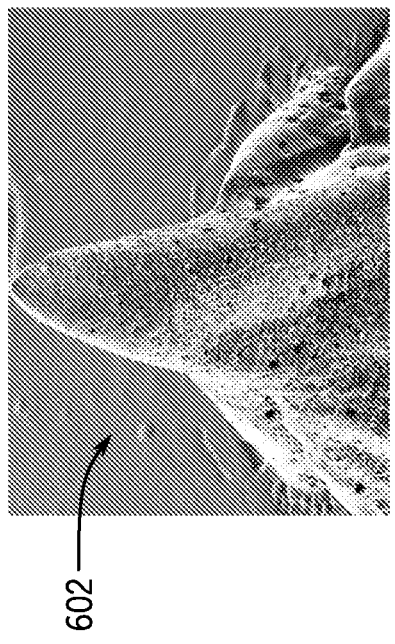
FIG. 6B is a detail view of a single microneedle of the microneedle array of FIG. 6A.
Figure 6A:
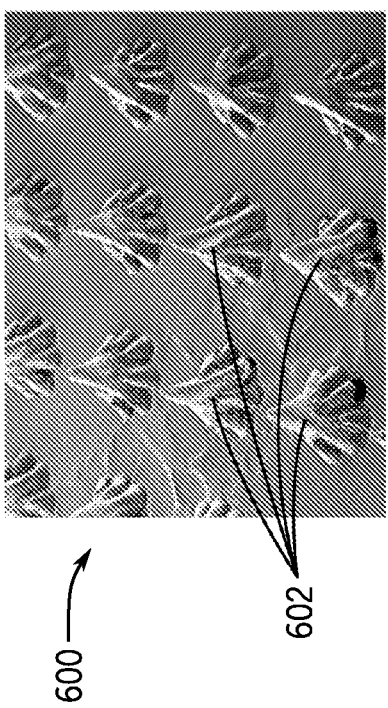
FIG. 6A is a perspective view of a microneedle array created using the emulsified composite solution of FIG. 5B.
Figure 6C:
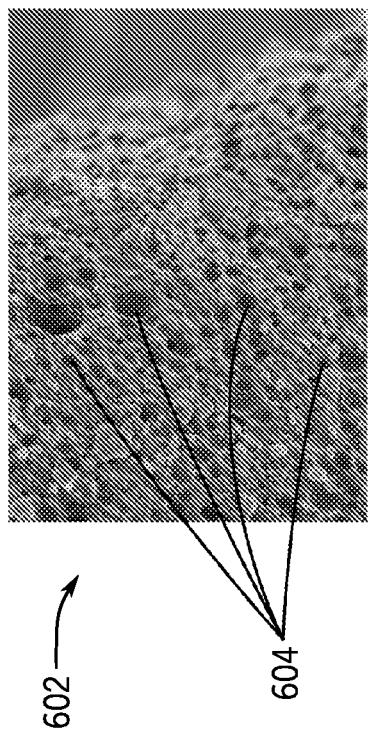
FIG. 6C is a detail view of the surface of the single microneedle of FIG. 6B.

Referring now to FIGS. 6A-6C, a macroPoSH microneedle array 600 including a plurality of macroPoSH microneedles 602 created using the emulsified composite solution 506 described above is shown. In some instances, the macroPoSH microneedle array 600 may be created using the methods described herein. In some instances, the macroPoSH microneedle array 600 can be created using any other type of suitable microneedle molding process.

Because the macroPoSH material has a Young's modulus significantly higher than that of skin, the macroPoSH microneedles 602 can be configured to effectively penetrate the skin of a subject during treatment. However, as best illustrated in FIGS. 6B and 6C, the surface of each macroPoSH microneedle 602 can be highly porous. For example, in some instances, pores 604 on the surface (and throughout the interior volume) of the macroPoSH microneedles 602 may range from 1 μm to 10 μm, as non-limiting examples.

Because of the high level of porosity of the macroPoSH microneedles 602, the drug solution micro-droplets 508 disposed throughout the macroPoSH microneedles 602 may be released upon penetration of the macroPoSH microneedles 602 into the skin of a subject. Thus, the macroPoSH microneedles 602 provide high level of hardness, capable of effectively penetrating the skin of the subject, while simultaneously allowing for larger amounts of drug solution to be administered to the subject than traditional hard microneedles.

Referring now to FIGS. 7A-7D, a process for creating a flexible microneedle patch is illustrated. As shown in FIG. 7A, a moldable microneedle material 700 may first be cast onto a microneedle mold 702. In some instances, the moldable microneedle material 700 may comprise the emulsified composite solution 506 described above. In other instances, the moldable microneedle material 700 may comprise any other suitable moldable material for creating hard microneedles (i.e., microneedles having a Young's modulus significantly higher than that of human skin).

Referring now to FIG. 7B, once the moldable microneedle material 700 is cast onto the microneedle mold 702, excess moldable microneedle material 700 may be removed from the microneedle mold 702, such that the moldable microneedle material 700 fills only microneedle-forming cavities 704 of the microneedle mold 702.

After the excess moldable microneedle material 700 has been removed, with the microneedle-forming cavities 704 filled with the moldable microneedle material 700, a flexible substrate polymer 706 may be cast onto the microneedle mold 702, as shown in FIG. 7C. Both the moldable microneedle material 700 and the flexible substrate polymer 706 may then be allowed to dry.

Once the moldable microneedle material 700 and the flexible substrate polymer 706 have dried, they may collectively form a flexible microneedle patch 708 having a plurality of microneedles 710 connected by a flexible back substrate 712. This flexible microneedle patch 708 may then be removed from the microneedle mold 702, as shown in FIG. 7D.

Figure 8A:
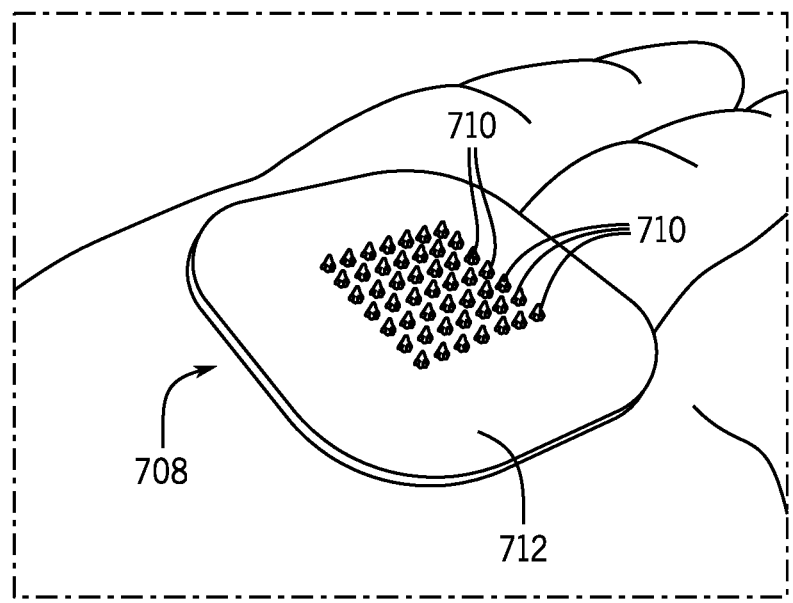
FIG. 8A is a perspective view of the flexible microneedle patch of FIG. 7D, shown in a flat position.
Figure 8B:
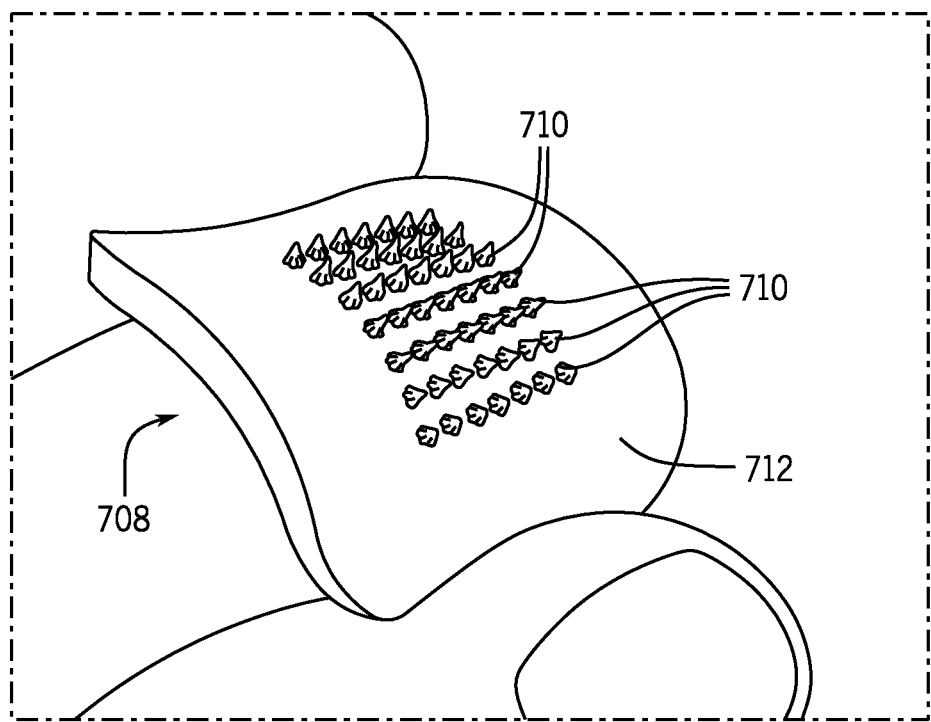
FIG. 8B is a perspective view of the flexible microneedle patch of FIG. 8A, shown in a bent position.

The flexibility of the flexible microneedle patch 708 (shown between FIGS. 8A and 8B) allows the flexible microneedle patch 708 to readily conform to any portion of the human body (e.g., arm, knee, neck, etc.), while the hardness of the microneedles 710 allows them to effectively penetrate the skin of a subject to permeate the skin for drug administration.

Figure 9:
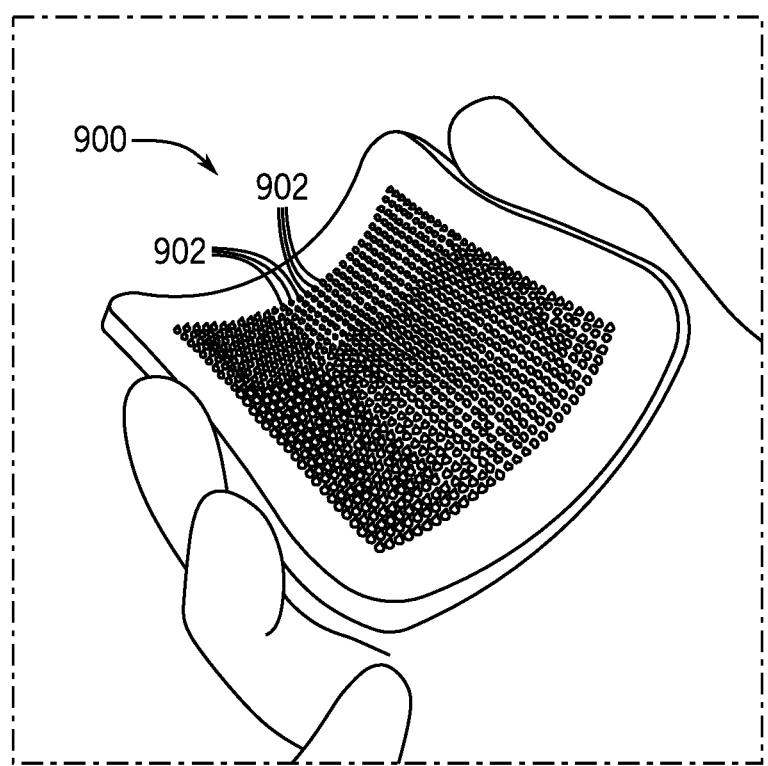
FIG. 9 is a perspective view of another flexible microneedle patch.

Further, using the above-described method (shown in FIGS. 7A-7B), flexible microneedle patches of varying sizing and including varying numbers of microneedles can be created. For example, FIG. 9 illustrates another flexible microneedle patch 900 that is larger, and includes several more microneedles 902, than the flexible microneedle patch 708. Accordingly, dosage and sizing can be adjusted accordingly for a given application.

Figure 10:
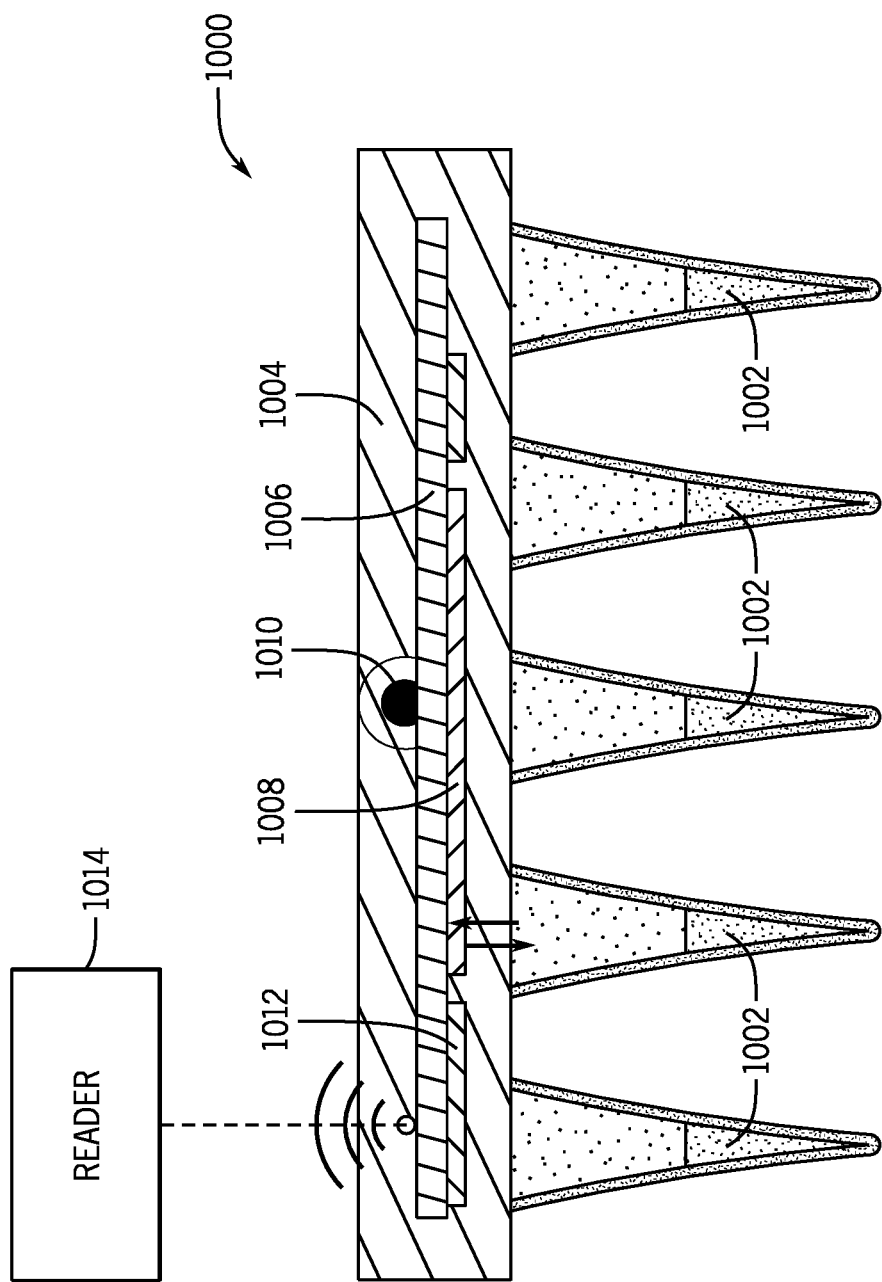
FIG. 10 is a cross-sectional view of another flexible microneedle patch containing embedded electronics.

Referring now to FIG. 10, another flexible microneedle patch 1000 is illustrated. Similar to the flexible microneedle patches 708, 900 described above, the flexible microneedle patch 1000 includes a plurality of microneedles 1002 connected by a flexible back substrate 1004. However, the flexible microneedle patch 1000 further includes an electronic chip 1006 embedded therein. The electronic chip 1006 may be flexible, wirelessly powered, and may be in communication with a sensor 1008, an LED light 1010, and a wireless communication device 1012.

The electronic chip 1006 may be configured to monitor the drug release rate through the plurality of microneedles 1002 using the sensor 1008. When the drug release rate has reached a predetermined level, the electronic chip 1006 may be configured to light up the LED light 1010 to alert the subject or user that the drug release rate has dropped below a predetermined threshold, or that the drug solution contained within flexible microneedle patch 1000 has been depleted.

The electronic chip 1006 may be configured to wirelessly transmit stored data and/or data acquired from the sensor 1008 to a reader 1014. For example, in some instances, the electronic chip 1006 may include an RF ID tag for identifying and/or tracing the type or dosage of the drug loaded onto the flexible microneedle patch 1000. In some other instances, the drug release rate of the flexible microneedle patch 1000 may be intermittently checked using the reader 1014. The reader 1014 may be a smart phone, a wearable electronic device, an RF ID tag reader, a laptop, or any other suitable wireless reader.

In some instances, the electronic chip 1006 may further be configured to control the drug release being administered from the flexible microneedle patch 1000 to the subject. For example, in some instances, the electronic chip 1006 may be in communication with a micropump (e.g., a piezoelectric pump) configured to supply the drug solution to the microneedles 1002.

In some other instances, the microneedles 1002 may comprise a thermosensitive material that exhibits a temperature dependent drug release profile. For example, the microneedles 1002 may be a thermo-responsive material, such as poly(N-isopropylacrylamide) (PNIPAAM). In these instances, the electronic chip 1006 may be in communication with a heating/cooling source (e.g., a Peltier thermoelectric heating or cooling patch, a resistive conductive heater, etc.) and be configured to modulate the temperature of the microneedles 1002 using the heating/cooling source to increase or decrease the drug release being administered to the subject.

In yet some other instances, the microneedles 1002 may comprise a hydrogel-based material, and the electronic chip 1006 may be configured to create a voltage difference between the microneedles 1002 and the skin, thereby allowing for control of the drug release through the microneedles 1002

Figure 11A:
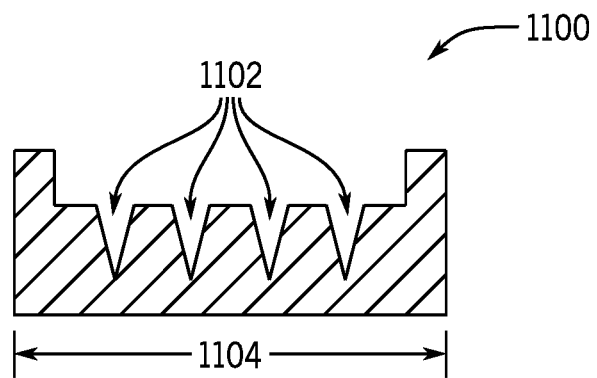
FIG. 11A is a stretchable microneedle cavity mold, shown in an unstretched position.
Figure 11B:
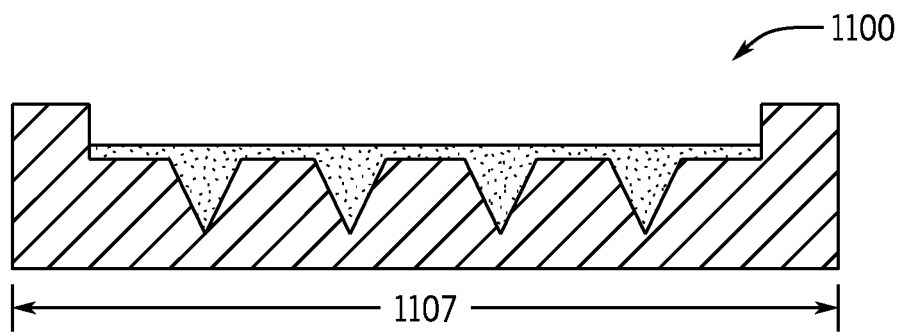
FIG. 11B is the stretchable microneedle cavity mold of FIG. 11A, shown in a stretched position with a microneedle material cast therein.
Figure 11C:
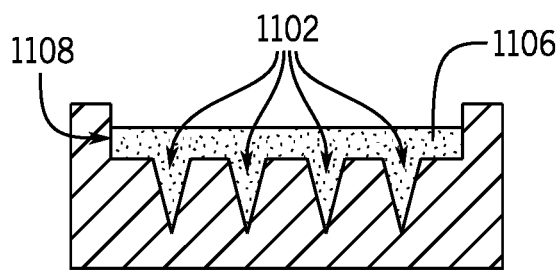
FIG. 11C is the stretchable microneedle cavity mold with the microneedle material cast therein of FIG. 11B, shown released to the unstretched position.

Referring now to FIGS. 11A-11C, a stretchable microneedle mold 1100 is illustrated. The stretchable microneedle mold 1100 includes a plurality of microneedle-forming cavities 1102, and may comprise a stretchable polymer.

As shown in FIG. 11A, the stretchable microneedle mold 1100 may have a resting length 1104 when the stretchable microneedle mold 1100 is unstretched. While casting a polymer 1106 into the stretchable microneedle mold 1100, the stretchable microneedle mold 1100 is stretched to a stretched length 1107, as shown in FIG. 11B. In some instances, the stretched length 1107 may be at least three times the resting length 1104. Stretching the stretchable microneedle mold 1100 allows for the polymer 1106, which may be a highly viscous solution, to more easily flow into microneedle-forming cavities 1102. In some instances, the polymer 1106 may additionally be rubbed onto the stretchable microneedle mold 1100 to ensure its penetration into the microneedle-forming cavities 1102.

With the polymer 1106 cast onto the stretchable microneedle mold 1100, the stretchable microneedle mold 1100 may then be released, such that it returns to its resting length 1104, as shown in FIG. 11C. With the stretchable microneedle mold 1100 in the resting position (shown in FIG. 11C), the polymer 1106 within the stretchable microneedle mold 1100 may be allowed to dry to create a microneedle array 1108.

When removing the microneedle array 1108 from the stretchable microneedle mold 1100, the stretchable microneedle mold 1100 may once again be stretched to allow for easy removal of the microneedle array 1108. In some instances, because the stretchable microneedle mold 1100 is stretched while casting the polymer 1106, the drying process may be controlled not include the application of excessive heating or vacuum pressure.

EXAMPLE

In one non-limiting study, the COL microneedle mold forming technique described above was used in the following exemplary procedure. First, a 2D drawing was used to fabricate a 3D structure. Here, the microneedle mold was engraved on a commonly used clear cast acrylic sheet using a $CO_2$ cutter Boss LS-1416 with maximum power of 60 W. The FTIR transmission spectrum of the clear cast acrylic sheet was shown to have a reasonable absorption, around 10.6 μm wavelength of the $CO_2$ laser responsible for the cutting of the sheet. Initially, the laser beam was auto focused on the surface of acrylic sheet.

The fabrication was performed by engraving lines that overlap only at their center cross point, as described above. Each line was engraved with the same laser power and engraving speed, which resulted in almost the same depth per run. However, as discussed above, the engraving depth at the center cross point was higher due to this point being traversed multiple times.

The engraved acrylic mold was then washed with isopropanol and distilled water to remove the dust and particles from the surface and engraved areas. A nitrogen gun was used to remove the excess water on the surface. The mold was then dried in an atmospheric oven at 80° C. for 30 minutes. In the next step, the mold's replicate was created by casting polydimethylsiloxane (PDMS) (with the ratio of 10:1 weight ratio of elastomer to curing agent) on the acrylic sheet. The PDMS-casted sheet was degassed and subsequently cured in the oven at 80° C. for two hours.

The PDMS microneedles were then detached from the acrylic mold and were treated with oxygen plasma to activate the surface of PDMS. The microneedles were then silanized with Tricholor (1H, 1H, 2H, 2H-perfluorooctyl) silane under vacuum in a desiccator overnight. Briefly, the sample was placed in a desiccator and 10 μL of the silane solution was dispensed on a piece of aluminum foil in the desiccator. The desiccator was then vacuumed and was kept in that condition overnight to complete the process. PDMS (with the ratio of 10:1) was cast (to create a mold) on the silanized microneedles followed by degassing and curing in an atmospheric oven. The silane layer created a barrier between PDMS microneedles and PDMS mold, thereby preventing them from bonding to each other and facilitating their detachment. The final PDMS mold was used to create microneedles from different polymers. Methods used for fabrication of polymer based microneedles are described below.

Characterization of the laser cutter was found to be an important factor in achieving desired the shapes and sizes of microneedles. FIG. 12A shows the engraved depth on an acrylic substrate for different laser power and speed settings. To fabricate the acrylic mold, two different speed settings of 5 mm/s and 10 mm/s were chosen. Later on, the effect of laser power on the engraved depth was evaluated (with 1% resolution). It was shown that the cutter started to engrave the acrylic surface at power levels greater than 5.4 W, which was 9% of the laser cutter's maximum power setting (60 W). Meanwhile, for power levels below 5.4 W, no engraving was observed.

Therefore, 5.4 W laser power (for the previously-mentioned speeds) was chosen to achieve fine engraving resolution and used for all fabricated microneedle acrylic molds in this example. Microneedles of different shape, size and angle were fabricated by altering three parameters of laser scanning speed, number of lines used to fabricate each needle, and length of the lines (see FIG. 12B).

Two different levels for the length of the lines (1 mm and 1.5 mm) and engraving speeds (5 mm/s and 10 mm/s) were considered in this experiment, which are elaborated in Table 1 below. Five levels were also considered for number of lines used to fabricate the Acrylic mold, which were 4, 6, 8, 10 and 12.

It was observed that the length of lines does not affect the height of needles considerably. However, longer lines leads to slightly sharper needles, which is likely a result of longer lines having a more stable laser beam at the cross-point.

Depending on the application of the needle, specific sizing of the needle may be required. Height and tip angle are two major characteristics of the microneedles. As shown in this experiment, these two factors, which are characterized in FIG. 12C, can be readily controlled by either changing the number of lines or engraving speed.

TABLE 1

Needle types based on fabrication parameters including engraving speed and length of the lines in COL design

| Microneedle Type | Engraving Speed (mm/s) | Length of Lines (mm) | Power (W) |
|---|---|---|---|
| MN-1 | 5 | 1 | 5.4 |
| MN-2 | 5 | 1.5 | 5.4 |
| MN-3 | 10 | 1 | 5.4 |
| MN-4 | 10 | 1.5 | 5.4 |

Figure 13:
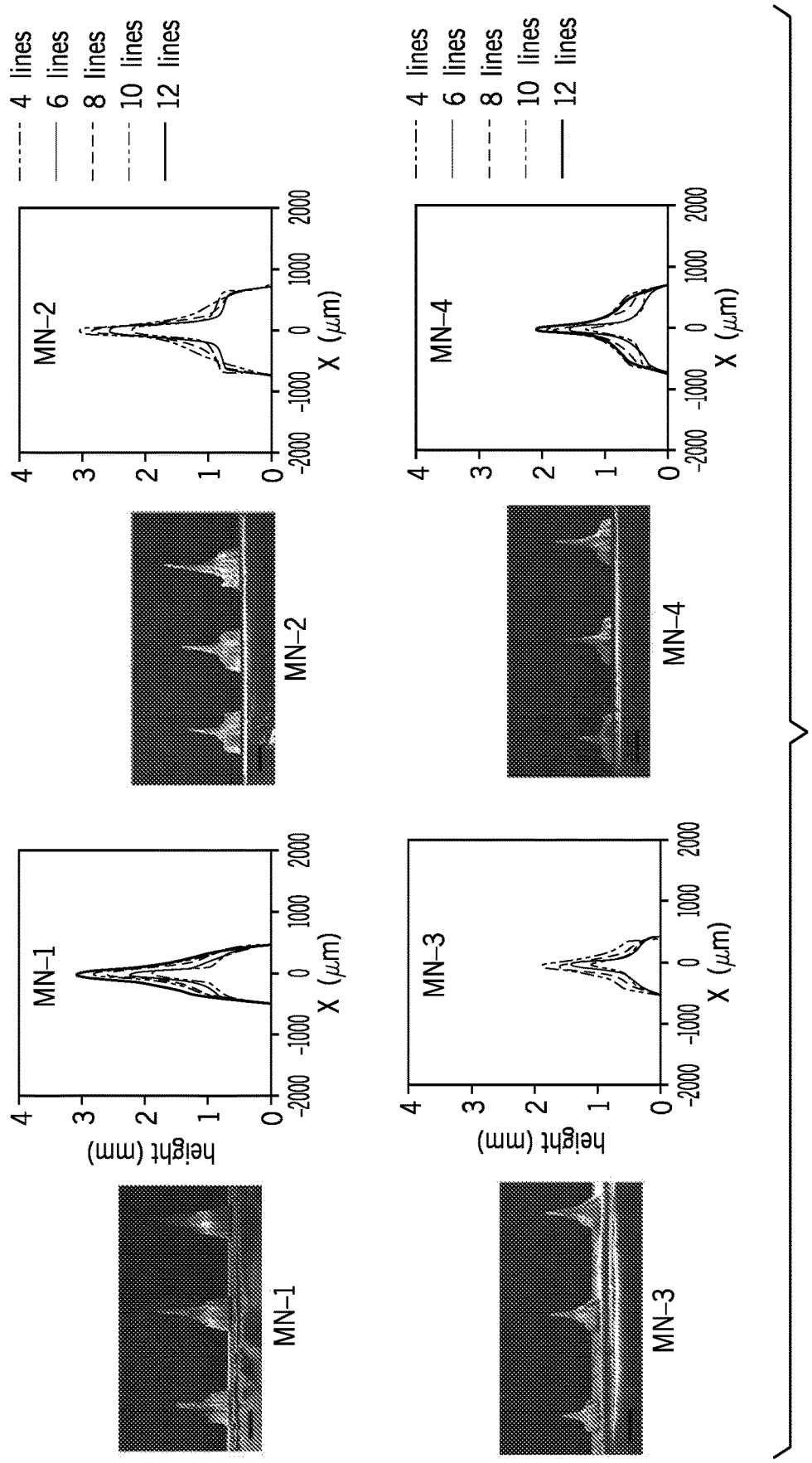
FIG. 13 is an illustration showing various shape of microneedles with different lengths and number of lines. SEM images (from left to right) are also shown for needles fabricated with 4, 6, and 8 lines.

To better illustrate the effect on the shape of the fabricated microneedles using the different above-mentioned factors, the profile of the fabricated needles were captured and quantified using image processing. FIG. 13 shows the shape of the resulted microneedles, where the first column shows the microneedles fabricated with 1 mm engraved lines and the second column shows the needles with 1.5 mm length of lines. As discussed above, the different line lengths did not differ in depth (or height of the needle) to a large extent due to the fact that the height of the needles are mostly dependent on the number of engraved lines. However, the length of the lines affect the overall shape of the needles where longer lines create sharper conical shape. Observably needles with higher height are achievable by simply increasing the number of lines to fabricate each needle.

Accordingly, needles of different heights and tip angles can be fabricated with the proposed technique and methods disclosed herein. In this experiment, as described above, the fabricated microneedle mold cavities had two parts: a head and a base. The head had a fine conical shape, suitable for microneedle applications, and the base had the above-described star-like shape. In order to separate these two parts, and just use the head of the microneedle mold, two sheets of Acrylic were placed on top of each other, bottom sheet was 5.5 mm and the top sheet was 1.5 mm clear cast acrylic sheet.

Subsequently, the laser cutter was used to engrave the sheets using the COL technique described herein. In this experiment, the engraving power was slightly increased up to 12% of the maximum power to compensate for the additional sheet. The top sheet was chosen to be thin enough to contain only the base part. These two sheets were then separated from each other using a razor blade (the sheets were weakly attached to each other at engraving points). Therefore, after removal of the top sheet, the bottom sheet contained only the head portion of the microneedles.

Figure 14A:
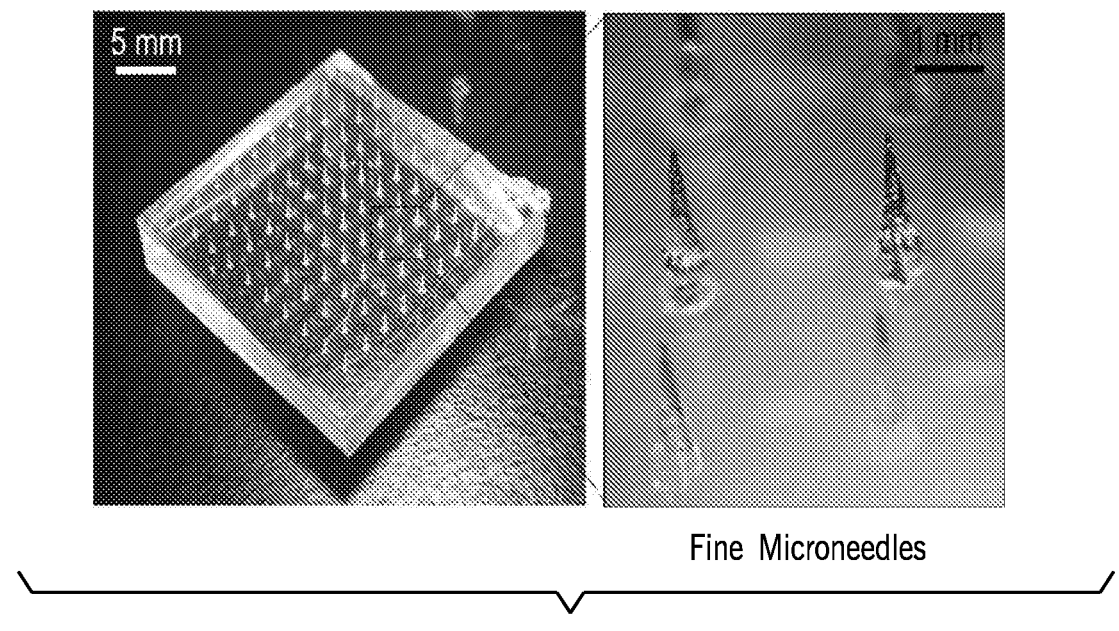
FIG. 14A is an illustration showing an array of fabricated microneedles

The bottom sheet was then used to fabricate PDMS microneedles (see FIG. 14A). Accordingly, the fabricated PDMS microneedles needle had a fine conical shape is achieved (FIG. 14A).

Figure 14B:
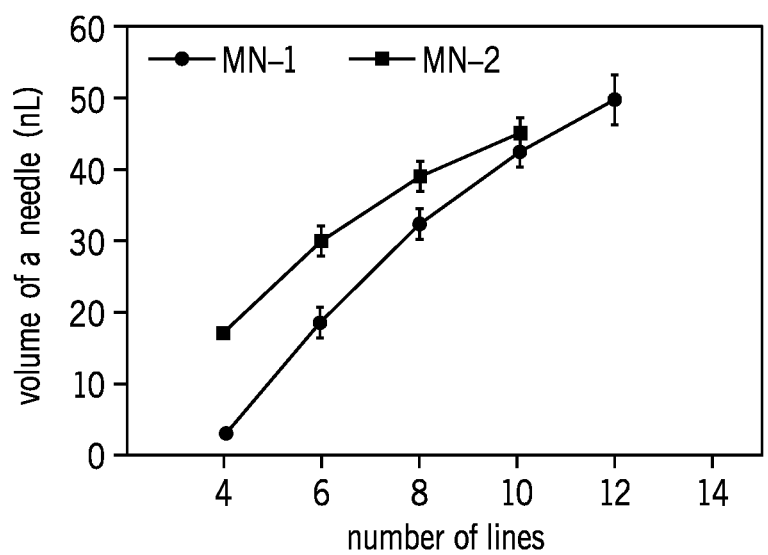
FIG. 14B is an illustration of the calculated volume of fine needles based on mold fabrication parameters.

The volume of each needle was then calculated based on the mold fabrication parameters (see FIG. 14B). This calculation provided an estimated amount of drug that each needle may carry.

Figure 15:
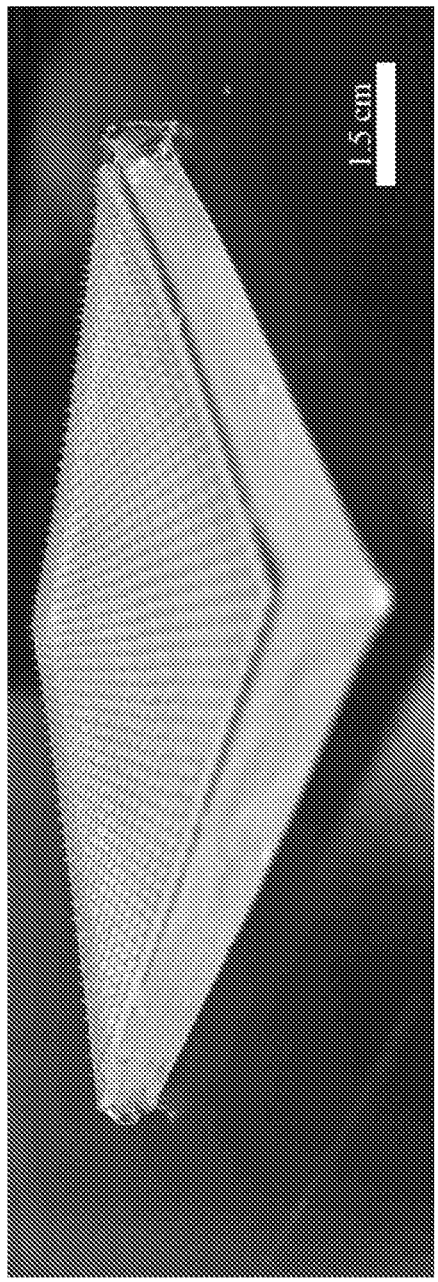
FIG. 15 is an illustration of a microneedle patch.

The usual commercial microneedle patch size is about 30-40 cm². The working platform of the laser cutting system used was 16"×12", thereby allowing fabrication of a microneedle patch with a common patch size. To make this point, a 6×6 cm2 patch was fabricated, including 1122 microneedles. This patch is shown in FIG. 15.

Degradable microneedles were fabricated using PVA polymer. PVA is a water-soluble polymer with wide practical application in a variety of fields including wound dressing, implants, cell encapsulation, drug-delivery systems, soft contact lenses, and dental applications due to its excellent chemical resistance and physical properties, low toxicity, and high biocompatibility. An aqueous solution of PVA can form hydrogels through cast-drying process, where PVA physically cross-links during the dehydration process.

Figure 16B:
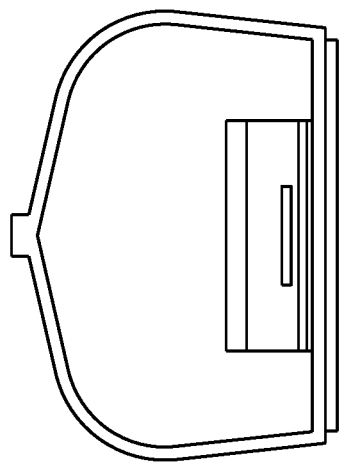
FIG. 16B is an illustration of the mold of FIG. 16A being submerged in a petri dish with a solution containing a drug model.
Figure 16C:
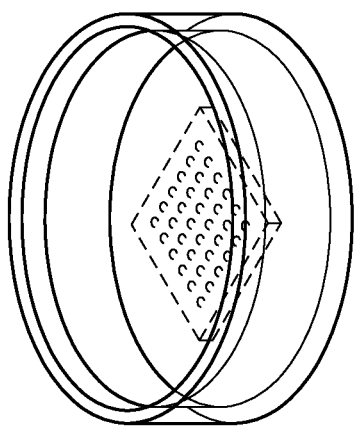
FIG. 16C is an illustration of the mold submerged in the petri dish placed inside a desiccator.
Figure 16A:
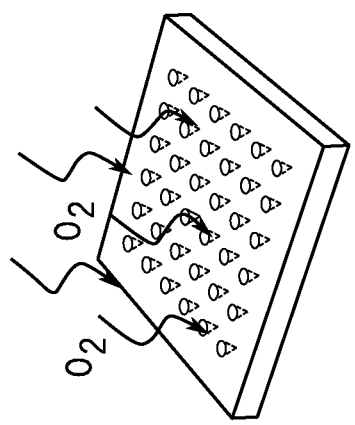
FIG. 16A is an illustration of a mold being oxygen plasma treated.
Figure 16D:
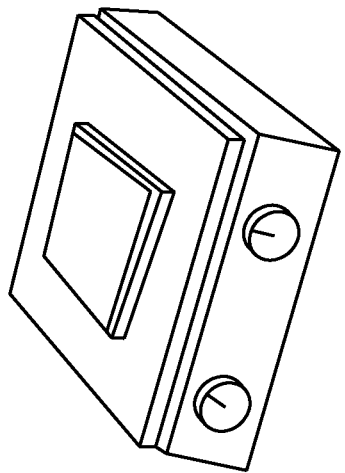
FIG. 16D is an illustration of the mold placed on a hot plate.
Figure 16E:
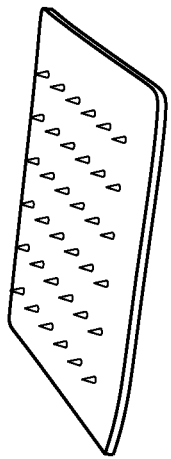
FIG. 16E is and illustration of a microneedle patch pulled off of the mold after complete drying.

The fabrication procedure followed is shown in FIGS. 16A-16E. Initially a solution 10% PVA was prepared by mixing PVA powder in distilled water. As a drug model, phenol red pH dye powder was added to the mixture to create 0.1% (weight/volume) concentration. The mixture was placed in oven at 50° C. for 5 hours to create a homogeneous solution. Next, the microneedle PDMS mold was oxygen plasma treated for 5 minutes. Plasma treating creates a hydrophilic surface that facilitates penetration of PVA (10%) solution into PDMS microneedles mold cavities (FIG. 16A). The mold was then submerged in the prepared PVA solution (FIG. 16B) and the sample was placed in a desiccator under vacuum condition for 7 days (FIG. 16C). This allowed the trapped air bubbles inside the mold cavities to come out and be replaced by PVA solution. Vacuum condition (for 5 days) also removes water moisture slowly and creates a dense PVA solution. To avoid the excessive time of 7 days, a vacuum oven could be used to remove the bubbles faster and make the solution dense in a few hours. Moreover if the drug is such that it does not degrade at slightly elevated temperatures, heat could also be applied to speed up the densification process. The mold was then placed on a hotplate at 40° C. to dry out and crosslink the PVA patch (FIG. 16D). After 5 hours, the PVA microneedle patch was hard enough to be removed from the microneedle mold (FIG. 16E). In some instances, the final drying step at 40° C. can be replaced by drying the microneedle patch in a dry desiccator at room temperature for 2 days, in case the drug is sensitive to elevated temperature.

Figure 16G:
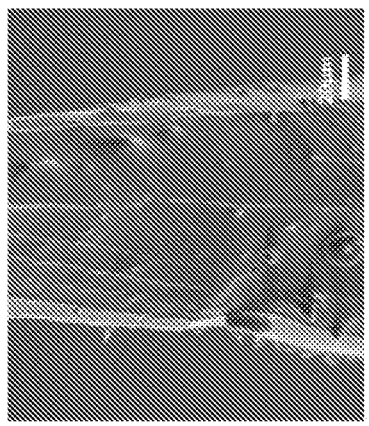
FIG. 16G is an SEM image of a PVA microneedle before drug release.
Figure 16I:
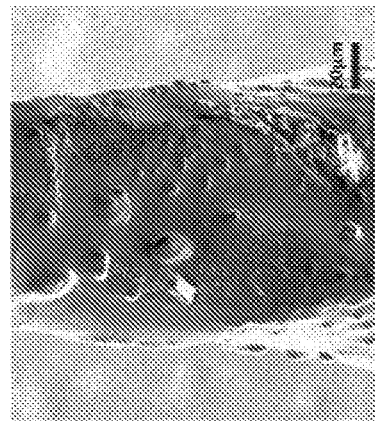
FIG. 16I is an SEM image of the PVA microneedle of FIG. 16G after drug release
Figure 16F:
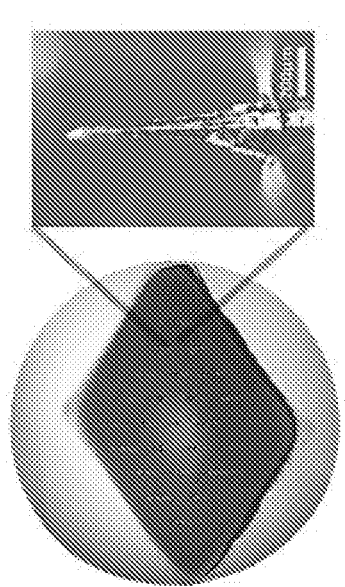
FIG. 16F is an image of a fabricated PVA microneedle patch.

The prepared PVA microneedle with this method showed adequate physical stability (FIG. 16F, the red color is due to phenol red). SEM images taken from the samples show the PVA needles have a smooth surface with minimum roughness and very low porosity (FIG. 16G). This shows the dense structure of the PVA with minimum air trapped inside the structure. To examine the drug release mechanism, the microneedle patch was immersed in phosphate buffered saline solution and placed inside an incubator. It was observed that phenol red dye, which served as the drug model, was released from the patch almost completely after one day, such that the patch becomes clear (FIG. 16H).

Figure 16H:
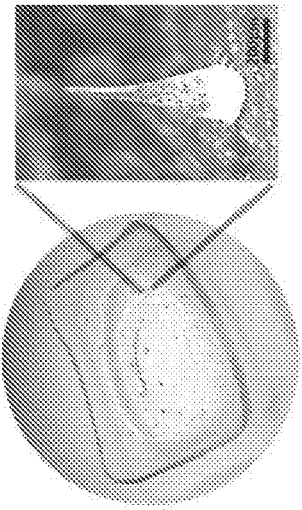
FIG. 16H is an image of the PVA microneedle patch of FIG. 16F after drug release.

However, the needles preserved their structure for several days in PBS (FIGS. 16H-16I). The increase in crystallization degree and hydrogen bonding may have been the main reasons for the low degradation rate of PVA microneedle patch (FIG. 16H). The degree of crystallization may also depend on the drying conditions. For example, slow drying at room temperature may allow the slow formation of crystal.

FTIR spectrum was acquired for PVA microneedle patch and compared with non-crosslinked PVA (FIG. 16J). An increase in the intensity of 1143 cm−1 peak was observed for PVA microneedle patch compared to non-crosslinked PVA, which was an indicator of the increase in the degree of crystallinity in physically crosslinked PVA. Moreover, the dehydration of free water may bring polymer chains close to each other due to the formation of additional hydrogen bonds (increase in the intensity of Hydroxyl group, FTIR (see FIG. 16J)) and this may provide enough crosslink points to facilitate the formation of polymer networks.

Figure 16M:
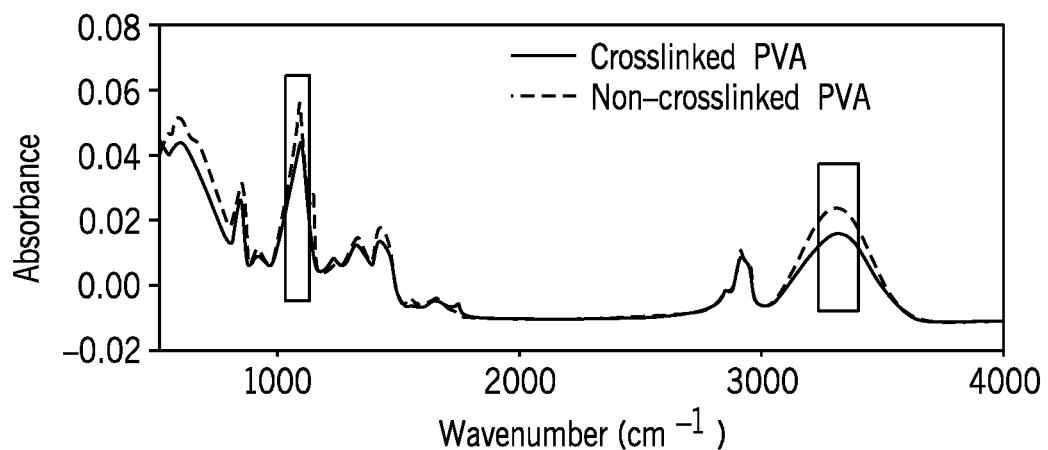
FIG. 16M is an illustration of the in vitro skin and release model.
Figure 16K:
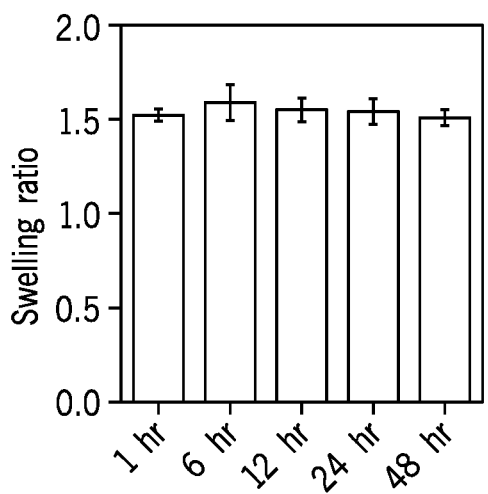
FIG. 16K is a chart showing swelling ratio of the PVA needles.
Figure 16L:
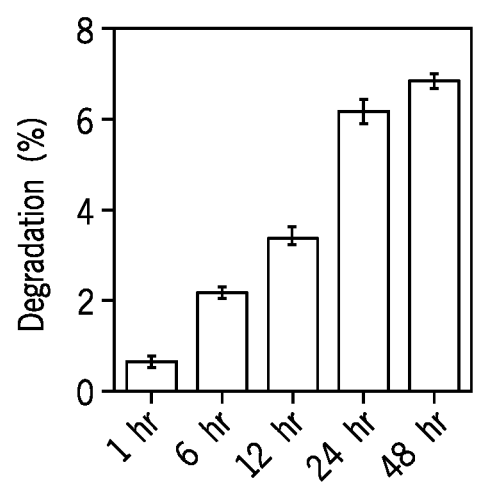
FIG. 16L is a chart showing degradation of the PVA needle in PBS (less than 8% after 48 hours).

Swelling and degradation tests were also carried out for the fabricated PVA microneedles (FIGS. 16K-16L). The weighed dry PVA Microneedle patch were immersed in the release medium (PBS, pH=7.4) at 37° C. for 1, 6, 12, 24 and 48 hours. At regular intervals, the swollen samples were wiped gently with paper and weighed, then samples were dried in room temperature to reach constant weight, and then immersed back into the PBS. The swelling degree and the degradation rate were calculated using Equation 1 and Equation 2 below:

$$\text{Degree of swelling} = \frac{M - M_i}{M_i} \times 100 \quad (1)$$

$$\text{Degradation rate} = \frac{M - M_d}{M_i} \times 100 \quad (2)$$

Where M is the weight of swollen sample, which were wiped with paper, $M_d$ is the dried mass of immersed sample in PBS, and $M_i$ is the initial dry mass of the sample.

Another important metric was the drug capacity of the microneedle patch. This depended on the volume of each microneedle, which depended on the fabrication parameters of the mold and the nature of polymer (see FIG. 14B). If the initial mixing ratio (mass/mass) of the drug to polymer and the density of the polymer and the drug is known, the amount of drug carried by each needle can be easily determined. Finally the number of needles in each patch will determine the total dose of delivered drug.

For in vitro drug release, a gelatin hydrogel derived from bovine skin, which is optically transparent and has similarity to the skin tissue, was used as a model tissue for drug release studies. Ten percent gelatin was placed in the refrigerator for solidification. Then, the polymer membrane (including the microneedles) was placed over on top of the hydrogel surface (FIG. 16M). A microneedle patch of 1×1 cm2 containing phenol dye was then pressed against the membrane surface to insert the microneedles into the gelatin hydrogel (FIG. 16M). The polymer membrane acted as a diffusion barrier and prevented the abrupt release of drug from microneedle's bulk PVA substrate into the underlying gelatin hydrogel.

Figure 16N:
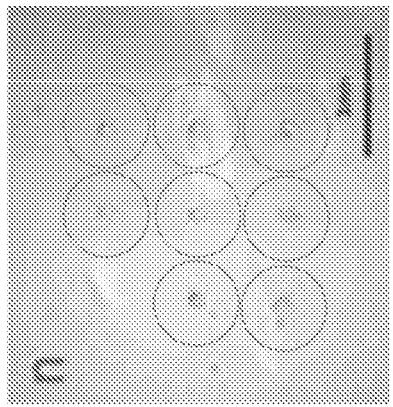
FIG. 16N is an image showing release of the drug into the hydrogel after 5 minutes.
Figure 16P:
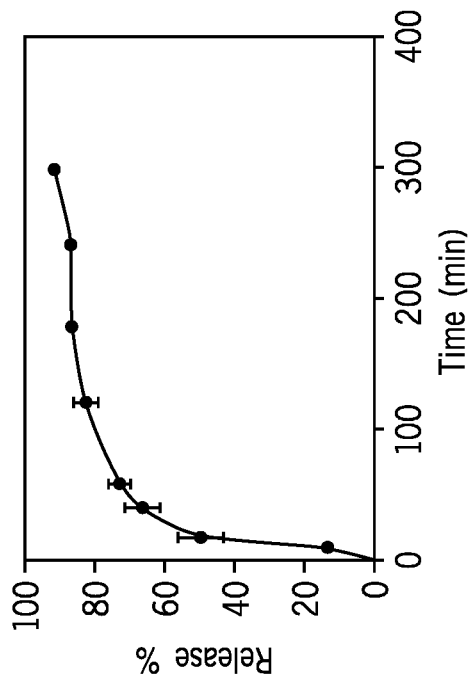
FIG. 16P is a chart showing a cumulative release model over time.
Figure 16M:
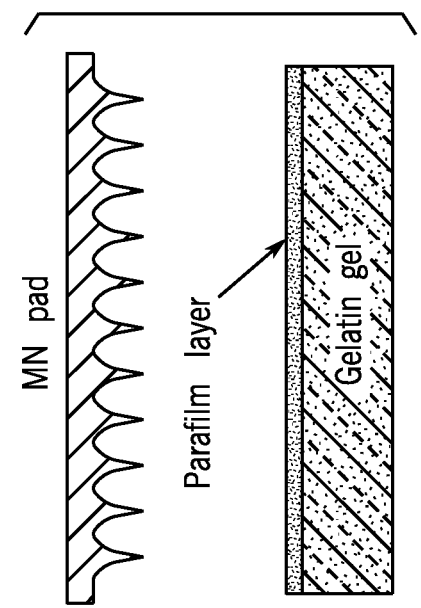
Figure 16O:
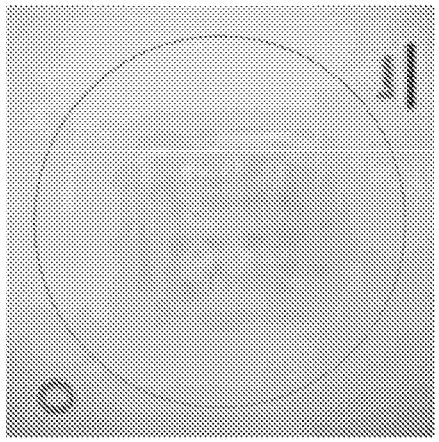
FIG. 16O is an image showing release of the drug after 5 hrs.

The phenol red was used as the model drug, and the standard curve was drawn to quantify the drug release. At each time stamp, the microneedle patch was detached from the hydrogel to stop further release (FIG. 16N-P). In FIGS. 16N and 16O, the release depth of the phenol red model drug released into the hydrogel is indicated generally by shaded circles surrounding the microholes created by the microneedle patch. By increasing the temperature, the gelatin liquefied and allowed for the measurement of the phenol red concentration released using UV-VIS spectroscopy at 450 nm wavelength. Almost half of the encapsulated phenol red inside microneedle was released in 20 minutes and the remaining was released in the next five hours (FIG. 16N-P). The test was performed at room temperature. Since most of the drug was released in the first hour, in a real scenario, the PVA microneedles could then be removed and disposed from the skin.

Drug release is either governed by the drug diffusion through hydrogel or by the degradation of the hydrogel. Thus, a swelling and degradation test was performed by incubating PVA microneedle patch in PBS for 48 hours at 37° C. to understand the mechanism of drug release from PVA (FIG. 16K-L). According to the degradation test result, only 6.81% of the PVA degraded during 48 hours (see FIG. 16L) thus polymer erosion did not play a significant role in drug release from PVA.

Figure 17B:
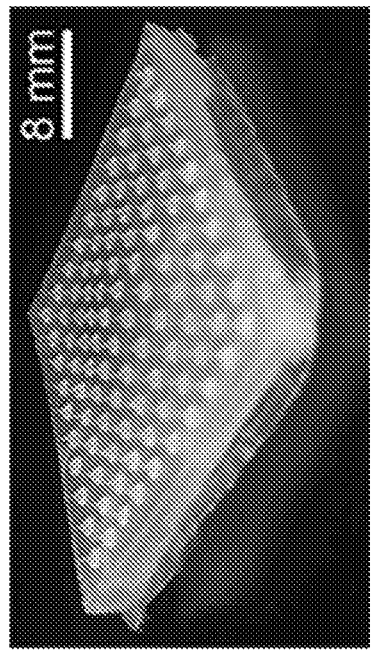
FIG. 17B is an image of a microneedle array made of poly-ε-caprolactone (PCL).
Figure 17A:
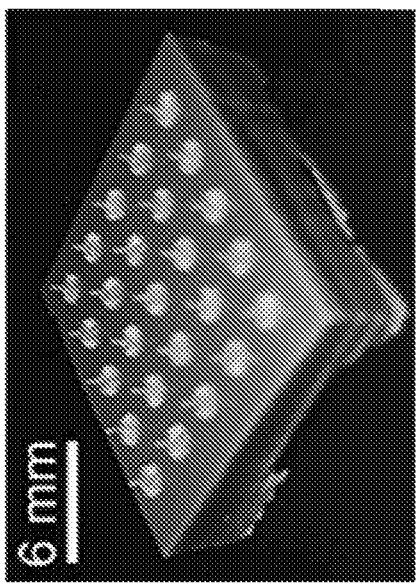
FIG. 17A is an image of a microneedle array made of photo curable resin.
Figure 17C:
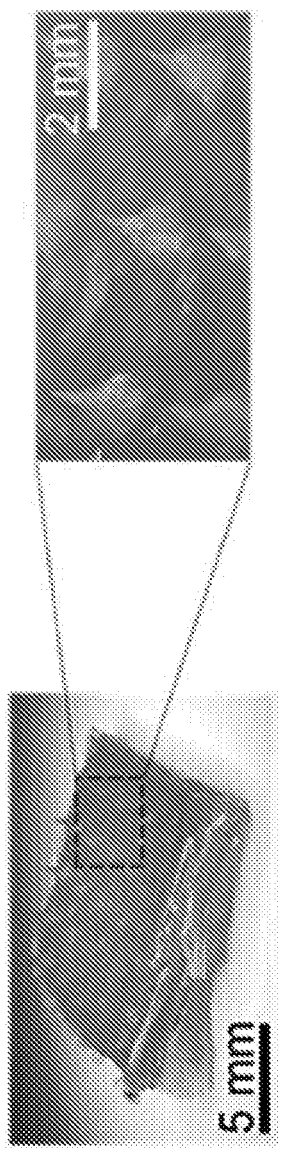
FIG. 17C is an image of a microneedle array made of Chitosan.

However, the high hydrophilic property of PVA led to high absorption of water, and, consequently, fast diffusion of drug in release media. In diffusion controlled release, the molecular size and weight play an important role. Phenol red is considered as the small molecule and its fast release can be explained by diffusion controlled release theory. After incubation of PVA microneedle in PBS, the free water penetrated into the empty regions of the polymer network until the equilibrium state was reached. Swelling of PVA continued for about one hour until the osmotic pressure equaled the forces of the crosslinking bonds that maintained the structure of the polymer network stable. At that time, no further water gain was observed. It should be appreciated that PVA microneedles were shown here as an example. Microneedles may alternatively be fabricated with different polymers including, for example, photo curable resins (shown in FIG. 17A, Poly-ε-caprolactone (PCL) (shown in FIG. 17B), and chitosan (shown in FIG. 17C).

Figure 18C:
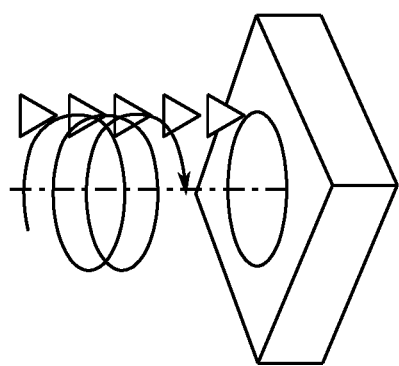
FIG. 18C is an illustration of helical laser drilling.

A variety of different ways of drilling by laser are within the scope of the disclosure. For example, laser drilling may be achieved using single shot drilling, trepanning, and helical drilling, as shown in FIGS. 18A-18C.

Figure 18B:
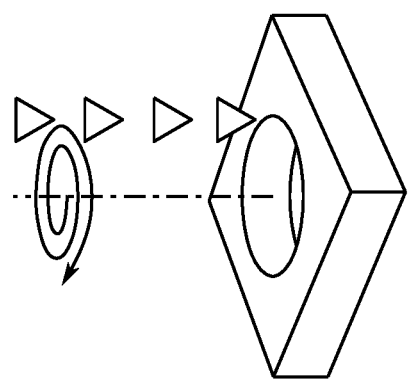
FIG. 18B is an illustration of trepanning laser drilling.
Figure 18A:
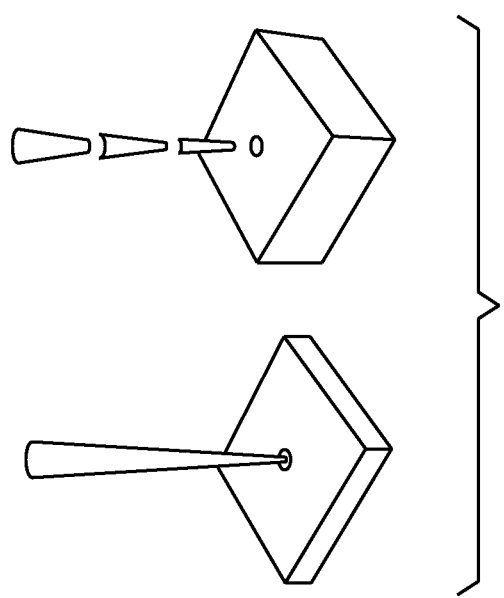
FIG. 18A is an illustration of single shot laser drilling.

One of the basic methods for drilling is single shot drilling, which is shown in FIG. 18A. This method can create a hole on the surface by focusing the laser beam at a point, and pumping the laser power in pulsed mode. This process can make a cylindrical and blunt hole which is generally narrow. Single shot drilling may not yield a conical hole where the base diameter is larger than the tip diameter. Single shot drilling may not allow for control of the base diameter of the needle. Conversely, the COL methods described herein allow for the implementation of needles with different base diameters, such as, for example, 1.5 mm and 1 mm wide base diameters.

Another method for drilling is trepanning, which is shown in FIG. 18B. This way of drilling results in a wider hole with a user-defined diameter. However there is no 3D shaping of the hole structure to allow for the formation of a conical shape. Helical drilling is similar to trepanning, as shown in FIG. 6c, such that it also suffers from the same disadvantages of the trepanning drilling. Conversely, the COL methods described herein translate a 2D design to a 3D conical structure. The COL technique can utilize a $CO_2$ laser cutting system to make the molds. In this implementation the only factor that limits the dimensions of the mold fabrication is the dimensions of the working platform of the laser.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing microneedles, the method comprising:
    creating at least one microneedle mold using laser ablation in a cross-over line pattern forming at least one cavity with a peaked cavity tip;
    casting a material onto the at least one microneedle mold to create at least one microneedle.

2. The method of claim 1, wherein the material is an emulsified, homogeneous mixture of a photocurable biocompatible resin and at least one of a concentrated drug solution and a dried drug powder.

3. The method of claim 2, wherein the material results in a macroporous structured hard material, after curing.

4. The method of claim 1, wherein creating the at least one microneedle mold using laser ablation in a cross-over line pattern comprises:
creating at least one primary forming mold using laser ablation in the cross-over line pattern;
casting a second material onto the at least one primary forming mold to create at least one secondary forming mold;
casting the second material onto the at least one secondary forming mold to create the at least one microneedle mold; and
removing the at least one microneedle mold from the at least one secondary forming mold.

5. The method of claim 4, further comprising plasma treating and silanizing the at least one secondary forming mold.

6. The method of claim 4, wherein the second material is a polymer.

7. The method of claim 1, further comprising placing the at least one microneedle and the at least one microneedle mold under vacuum to densify the at least one microneedle.

8. The method of claim 1, wherein the peaked cavity tip includes an angled wall.

9. The method of claim 8, wherein the peaked cavity tip is generally conically shaped.

10. The method of claim 1, wherein the creating the at least one microneedle mold using laser ablation in the cross-over line pattern includes forming a plurality of cavities in the microneedle mold, each cavity including a peaked cavity tip, the plurality of cavities being disconnected in the microneedle mold.

11. A method for producing microneedles, the method comprising:
creating at least one microneedle mold using laser ablation in a cross-over line pattern forming at least one generally conically-shaped cavity;
casting a material onto the at least one microneedle mold to create at least one microneedle.

12. The method of claim 11, wherein the material is an emulsified, homogeneous mixture of a photocurable biocompatible resin and at least one of a concentrated drug solution and a dried drug powder.

13. The method of claim 12, wherein the material results in a macroporous structured hard material, after curing.

14. The method of claim 11, wherein creating the at least one microneedle mold using laser ablation in a cross-over line pattern comprises:
creating at least one primary forming mold using laser ablation in the cross-over line pattern;
casting a second material onto the at least one primary forming mold to create at least one secondary forming mold;
casting the second material onto the at least one secondary forming mold to create the at least one microneedle mold; and
removing the at least one microneedle mold from the at least one secondary forming mold.

15. The method of claim 14, further comprising plasma treating and silanizing the at least one secondary forming mold.

16. The method of claim 14, wherein the second material is a polymer.

17. The method of claim 11, further comprising placing the at least one microneedle and the at least one microneedle mold under vacuum to densify the at least one microneedle.

18. The method of claim 11, wherein the generally conically-shaped cavity includes a peaked cavity tip.

19. The method of claim 18, wherein the peaked cavity tip includes at least one angled wall.

20. The method of claim 11, wherein the creating the at least one microneedle mold using laser ablation in the cross-over line pattern includes forming a plurality of cavities in the microneedle mold, each cavity including a peaked cavity tip, the plurality of cavities being disconnected in the microneedle mold.

21. A method for producing microneedles, the method comprising:
creating at least one microneedle mold using laser ablation in a cross-over line pattern forming a plurality of cavities in the microneedle mold, the plurality of cavities being disconnected in the microneedle mold;
casting a material onto the at least one microneedle mold to create at least one microneedle.

22. The method of claim 21, wherein the material is an emulsified, homogeneous mixture of a photocurable biocompatible resin and at least one of a concentrated drug solution and a dried drug powder.

23. The method of claim 22, wherein the material results in a macroporous structured hard material, after curing.

24. The method of claim 21, wherein creating the at least one microneedle mold using laser ablation in a cross-over line pattern comprises:
creating at least one primary forming mold using laser ablation in the cross-over line pattern;
casting a second material onto the at least one primary forming mold to create at least one secondary forming mold;
casting the second material onto the at least one secondary forming mold to create the at least one microneedle mold; and
removing the at least one microneedle mold from the at least one secondary forming mold.

25. The method of claim 24, further comprising plasma treating and silanizing the at least one secondary forming mold.

26. The method of claim 24, wherein the second material is a polymer.

27. The method of claim 21, further comprising placing the at least one microneedle and the at least one microneedle mold under vacuum to densify the at least one microneedle.

28. The method of claim 21, wherein each of the plurality of cavities is generally conically-shaped.

29. The method of claim 21, wherein each of the plurality of cavities includes a peaked cavity tip.

30. The method of claim 29, wherein the peaked cavity tip includes at least one angled wall.

* * * * *